US010465170B2

(12) United States Patent
Peeples et al.

(10) Patent No.: US 10,465,170 B2
(45) Date of Patent: Nov. 5, 2019

(54) LIVE ATTENUATED VACCINES FOR PNEUMOVIRUSES AND RELATED METHODS AND MATERIALS

(71) Applicants: RESEARCH INSTITUTE AT NATIONWIDE CHILDREN'S HOSPITAL, Columbus, OH (US); OHIO STATE INNOVATION FOUNDATION, Columbus, OH (US)

(72) Inventors: Mark E. Peeples, Bexley, OH (US); Jianrong Li, Dublin, OH (US); Hui Cai, Columbus, OH (US); Rongzhang Wang, Columbus, OH (US)

(73) Assignees: Ohio State Innovation Foundation, Columbus, OH (US); Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 15/552,212

(22) PCT Filed: Feb. 22, 2016

(86) PCT No.: PCT/US2016/018975

§ 371 (c)(1),
(2) Date: Aug. 18, 2017

(87) PCT Pub. No.: WO2016/134378

PCT Pub. Date: Aug. 25, 2016

(65) Prior Publication Data

US 2018/0066238 A1 Mar. 8, 2018

Related U.S. Application Data

(60) Provisional application No. 62/118,752, filed on Feb. 20, 2015.

(51) Int. Cl.

| | |
|---|---|
| ***C07K 14/005*** | (2006.01) |
| ***A61K 39/12*** | (2006.01) |
| ***C12N 15/86*** | (2006.01) |
| ***C12N 7/04*** | (2006.01) |
| ***C12N 7/00*** | (2006.01) |
| *A61K 39/00* | (2006.01) |

(52) U.S. Cl.

CPC .............. *C12N 7/045* (2013.01); *A61K 39/12* (2013.01); *C07K 14/005* (2013.01); *C12N 7/00* (2013.01); *C12N 15/86* (2013.01); *A61K 2039/5254* (2013.01); *C07K 2319/23* (2013.01); *C12N 2760/18522* (2013.01); *C12N 2760/18534* (2013.01); *C12N 2760/18562* (2013.01)

(58) Field of Classification Search

None

See application file for complete search history.

(56) References Cited

U.S. PATENT DOCUMENTS

| | | | | |
|---|---|---|---|---|
| 7,205,013 | B2 | 4/2007 | Jin et al. | |
| 2002/0119446 | A1 | 8/2002 | Wertz et al. | |
| 2004/0241188 | A1 * | 12/2004 | Collins ................ | A61K 39/155 424/199.1 |
| 2012/0308602 | A1 | 12/2012 | Jin et al. | |

OTHER PUBLICATIONS

Tang et al. Requirement of Cysteines and Length of the Human Respiratory Syncytial Virus M2-1 Protein for Protein Function and Virus Viability. J. Virol. Dec. 2001, vol. 75, p. 11328-11335.*

Tang et al. Requirement of Cysteines and Length of the Human Respiratory Syncytial Virus M2-1 Protein for Protein Function and Virus Viability. J. Virol. 2001, 75(23): 11328-11335.*

Hardy et al. The Cys3-His1 Motif of the Respiratory Syncytial Virus M2-1 Protein Is Essential for Protein Function. J. Virol. 2000, 74(13): 5880-5885.*

International Search Report and Written Opinion issued in PCT/US2016/018975, dated Apr. 29, 2016, 12 pages.

Jin et al. "Requirement of Cysteines and Length of the Human Respiratory Syncytial Virus N2-1 Protein for Protein Function and Virus Viablity," Journal of Virology, Dec. 1, 2001, vol. 75, Issue 23, pp. 11328-11335.

* cited by examiner

*Primary Examiner* — Nianxiang Zou

(74) *Attorney, Agent, or Firm* — Faegre Baker Daniels LLP

(57) ABSTRACT

Described herein are mutant *pneumoviruses* comprising a nucleotide sequence which encodes a mutated zinc binding motif in an M2-1 protein of the *pneumovirus*, wherein the zinc binding motif is mutated relative to wild-type *pneumovirus*. The mutant *pneumoviruses* described herein grow to high titer in cell culture, are genetically stable, are attenuated in vitro and in vivo, and are highly immunogenic. Also described herein are vaccines and vaccine compositions comprising the live attenuated mutant *pneumoviruses*. Vaccine compositions can further comprise a pharmaceutically acceptable carrier, vehicle, excipient, and/or adjuvant. Methods for inducing a protective immune response in a subject against a *pneumovirus* infection are also described and disclosed. The vaccine compositions and methods described herein can be used to prevent *metapneumovirus* and respiratory syncytial virus infection in humans, respiratory syncytial virus infection in cattle, avian *metapneumovirus* infection in various avian species, and pneumonia virus of mice in rodents.

17 Claims, 17 Drawing Sheets

Specification includes a Sequence Listing.

|              | Day 1 | Day 2 | Day 3 |
|--------------|-------|-------|-------|
| rgRSV        |       |       |       |
| rgRSV-C21S   |       |       |       |
| rgRSV-H25L   |       |       |       |

LIVE ATTENUATED VACCINES FOR PNEUMOVIRUSES AND RELATED METHODS AND MATERIALS

CROSS-REFERENCE TO RELATED APPLICATIONS

This application is a U.S. National Phase application of International Patent Application No. PCT/US2016/08975 filed Feb. 22, 2016 which claims the benefit of United States Provisional Application No. 62/118,752, filed on Feb. 20, 2015, each of which is expressly incorporated herein by reference in its entirety for all purposes.

STATEMENT REGARDING FEDERALLY SPONSORED RESEARCH

This invention was made with government support under Grant No. R01AI090060 awarded by National Institute of Allergy and Infectious Diseases (NIAID), National Institutes of Health. The government has certain rights in the invention.

SEQUENCE LISTING

The instant application contains a Sequence Listing which has been submitted via EFS-web and is hereby incorporated by reference in its entirety. The ASCII copy, created on Feb. 18, 2016, is named RINCH02WOU1_SL.txt, and is 15,400 bytes in size.

BACKGROUND OF THE INVENTION

The pneumoviruses include many important human and animal pathogens, including human respiratory syncytial virus (hRSV), bovine RSV, human metapneumovirus (hMPV), avian MPV, and pneumovirus of mice. Among these viruses, hRSV and hMPV are the leading causes of acute respiratory tract infection in infants and children. Despite major efforts, there is no antiviral or vaccine to help combat these diseases.

First discovered in 1956 as a lower respiratory tract pathogen of children in their first year of life, human respiratory syncytial virus is an enveloped, negative-sense single-stranded RNA virus belonging to the Pneumovirus genus within the Pneumovirinae subfamily of the family Paramyxoviridae. hRSV is a major cause of lower respiratory tract infections, most commonly resulting in mild respiratory tract disease. However, infection with hRSV may result in severe bronchiolitis and pneumonia. In industrialized countries, hRSV accounts for up to 70% of hospitalized bronchiolitis cases. Worldwide, hRSV is estimated to cause 199,000 deaths annually in children less than 5 years.

Bovine respiratory syncytial virus (bRSV) is closely related to hRSV, although there is no evidence that cross-species transmission between cattle and humans occurs. bRSV is considered a component of the bovine respiratory disease complex, and infects cattle of all ages, although suckling calves often experience the most severe disease. Serologic surveys indicate that bRSV is a very common virus in cattle populations worldwide.

Human metapneumovirus, first characterized in 2001 in the Netherlands, belongs to the *Metapneumovirus* genus within the Pneumovirinae subfamily of the family Paramyxoviridae. Soon after its discovery, hMPV was recognized as a globally prevalent pathogen, likely having been causing respiratory illnesses for at least 50 years worldwide.

A negative-sense single-stranded RNA virus, hMPV has been isolated from individuals of all ages with acute respiratory tract infection, especially in infants, children, the elderly, and immunocompromised individuals. hMPV infection is recognized as a leading cause of respiratory tract infection in the first years of life with symptoms similar to that of hRSV infection, including mild respiratory problems to severe coughs, bronchiolitis, and pneumonia. Transmission likely occurs through contact with contaminated secretions, and via droplet, aerosol, or fomite vectors. Epidemiological studies suggest that 5 to 15% of all respiratory tract infection in infants and young children are caused by hMPV, a proportion second only to that of hRSV.

The only other member in the genus *Metapneumovirus* is avian metapneumovirus (aMPV), also known as avian pneumovirus or Turkey Rhinotracheitis, is an economically important pathogen that causes acute respiratory disease in turkeys, and has been associated with swollen head syndrome in broiler chicken breeds as well as egg production losses in laying chicken breeds. First detected in turkeys in South Africa in the late 1970s, aMPV has since spread to all major poultry-producing areas in the world, except for Australia. In addition to affecting turkeys and chickens, aMPV has been detected in pheasants, Muscovy ducks, and guinea fowl. Epidemiologic studies provide evidence for the circulation of aMPV in wild birds, particularly water-associated species. Experimental studies have shown that turkeys may also be susceptible to hMPV. Infection with aMPV is often complicated by secondary bacterial infections, leading to high economic losses.

The genome of hMPV is a non-segmented negative-sense (NNS) RNA, with size ranging from 13,280 to 13,378 nucleotides, and contains 8 genes which encode for 9 proteins in the order of 3'-N-P-M-F-M2-SH-G-L-5'. Like all NNS RNA viruses, the genomic RNA is completely encapsulated by nucleoprotein (N), forming the N-RNA complex that serves as a template for genome replication and mRNA transcription. During replication, the RNA dependent RNA polymerase (RdRp) enters at the extreme 3' end of the genome and synthesizes full-length complementary antigenome, which in turn serves as template for synthesis of full-length progeny genome. During transcription, RdRp copies the genomic RNA template to synthesize a short uncapped leader RNA, and capped, methylated, and polyadenylated mRNAs that encode all viral proteins. The components of RdRp of *Paramyxovirinae* subfamily (family *Paramyxoviridae*), *Rhabdoviridae*, and *Bornaviridae* include the large (L) protein catalytic subunit and phosphoprotein (P) cofactor. The RdRp of the Pneumovirinae subfamily of the family *Paramyxoviridae* requires the M2-1 protein as an additional cofactor, whereas the *Filoviridae* (such as Ebola virus and Marburg virus) polymerase requires VP30 as an additional cofactor. Both the M2-1 protein of pneumoviruses and VP30 protein of filoviruses are typical zinc binding proteins thought to play many critical regulatory roles in RNA synthesis and processing via poorly understood mechanisms.

Metal ions were shown to be integrated in several gene regulatory proteins as early as the 1970s. Among them, zinc is an important structural component of proteins involved in nucleic acid binding and gene regulation. Zinc binding motifs, including CCHH, CCHC and CCCH, are often involved in transcriptional and translational processes. Many viruses encode their own zinc binding proteins that regulate viral replication and/or pathogenesis, such as NS5A protein of hepatitis C, almost all retroviral nucleocapsid proteins, which comprise one or two copies of a zinc finger motif essential for viral replication, the V proteins of many paramyxoviruses, and the VP30 protein of Ebola.

The M2-1 protein is unique to all known pneumoviruses. The current understanding of the functions of M2-1 proteins comes predominantly from studies of the hRSV M2-1 protein. The hRSV M2-1 functions as a transcriptional elongation factor and anti-terminator that enhances read-through of intergenic junctions. Thus, M2-1 is essential for synthesis of full-length mRNAs and polycistronic mRNAs. The hRSV M2-1 was found to be an RNA binding protein, although its RNA binding specificity is controversial. Recent NMR studies showed that the RSV M2-1 core domain preferentially recognizes poly-A tails of viral mRNAs. M2-1 likely binds nascent mRNA transcripts, preventing premature termination through stabilization of the transcription complex and inhibition of RNA secondary structure formation. Additionally, hRSV M2-1 was shown to interact with the N, P, and L proteins.

SUMMARY OF THE INVENTION

Described herein are mutant pneumoviruses comprising a mutated zinc binding motif in an M2-1 protein of the pneumovirus, wherein at least one amino acid of the zinc binding motif is mutated relative to wild-type pneumovirus. The mutant pneumoviruses described herein grow to high titer in cell culture, are genetically stable, are attenuated in vitro and in vivo, and are highly immunogenic. Also described herein are vaccine compositions, including vaccines, comprising the live attenuated mutant pneumoviruses provided herein. Vaccine compositions described herein may further comprise a pharmaceutically acceptable carrier, vehicle, excipient, and/or adjuvant. Methods for inducing a protective immune response in a subject against a pneumovirus infection are also described and disclosed. The vaccine compositions and methods described herein can be used to prevent metapneumovirus and respiratory syncytial virus infection in humans, respiratory syncytial virus infection in cattle, avian metapneumovirus infection in various avian species, and pneumonia virus of mice in rodents.

In a particular embodiment described herein is a mutant pneumovirus comprising a mutated zinc binding domain in an M2-1 protein of the pneumovirus, wherein at least one amino acid of the zinc binding domain is mutated relative to wildtype pneumovirus. In certain embodiments, the amino acid mutation in the zinc binding domain is non-lethal and at least partially inhibits zinc binding activity of the M2-1 protein or abolishes zinc binding activity of the M2-1 protein. In certain embodiments, the at least one amino acid mutation occurs at an amino acid selected from the group consisting of C7, C15, C21, and H25.

In another embodiment described herein is a vaccine composition comprising a mutant pneumovirus described herein. In certain embodiments, the vaccine composition is a live attenuate vaccine.

In yet another particular embodiment described herein is a method for inducing a protective immune response in a subject, comprising administering to the subject an immunologically effective dose of a vaccine composition described and disclosed herein.

In still another particular embodiment described herein is a method for preparing a vaccine composition described and disclosed herein comprising mixing a mutant pneumovirus described and disclosed herein with at least one of a pharmaceutically acceptable carrier, a pharmaceutically acceptable vehicle, a pharmaceutically acceptable excipient, and a pharmaceutically acceptable adjuvant. In certain embodiments, the vaccine composition is formulated for administration via an administration route selected from the group consisting of intranasal administration, subcutaneous administration, intramuscular administration, intradermal administration, and oral administration.

In another embodiment described herein is a kit comprising a vaccine composition described and disclosed herein and at least one container.

BRIEF DESCRIPTION OF THE DRAWINGS

The patent or application file may contain one or more drawings executed in color and/or one or more photographs.

Figure 4A:
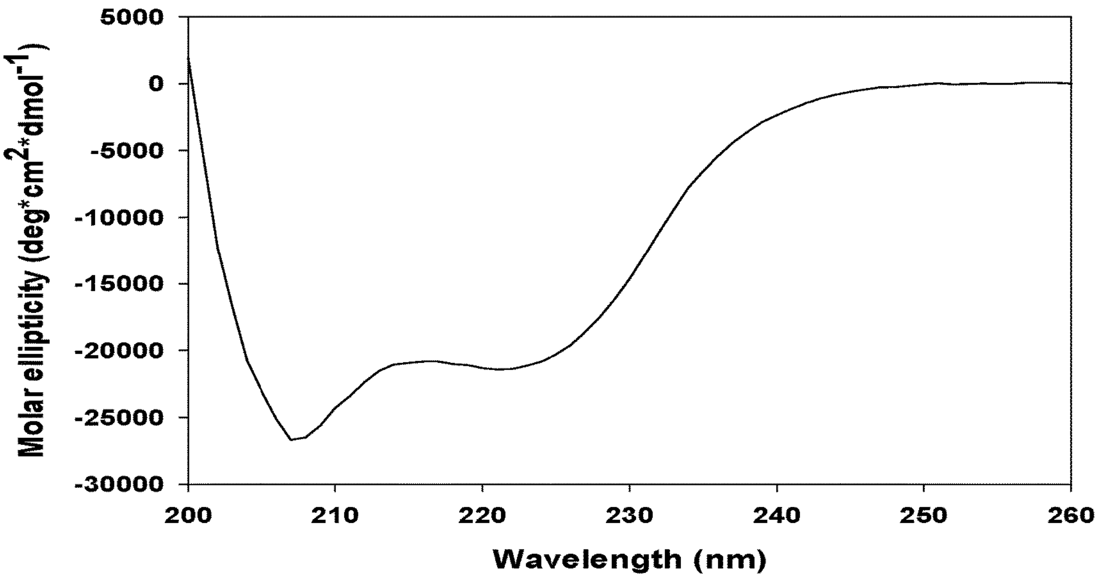
FIG. 4A: Circular Dichroism (CD) spectroscopic analysis of M2-1 protein. 2 μM M2-1 protein was analyzed by UV spectropolarimeter at a wavelength range of 190-260 nm at a scanning speed of 50 nm per min. α-helical signal was detected with two negative maximums at 208 nm and 222 nm using a CD spectroscopy analysis. The secondary structure of hMPV M2-1 at pH 7.4 and 20° C. was dominated by the ordered α-helices. Data were average of ten individual readings.
Figure 4B:
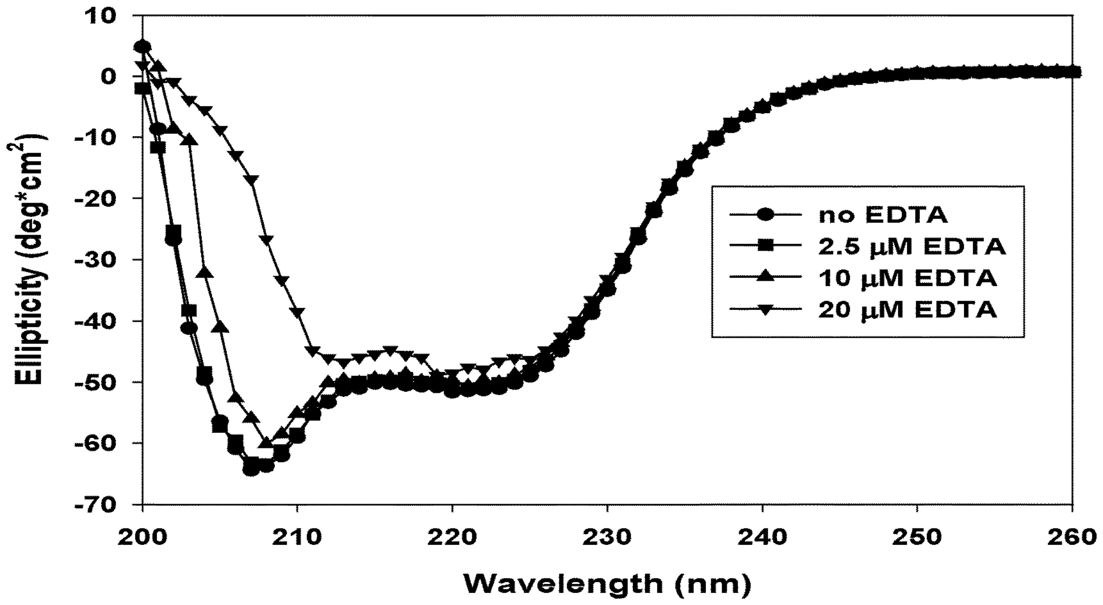

FIG. 4B: Alteration of M2-1 structure by EDTA 2 μM of M2-1 protein was incubated with increasing concentration of EDTA, and CD spectra were recorded. α-helical content gradually decreased when the concentration of EDTA increased from 0 to 20 μM. At the maximum metal chelation concentration (20 μM EDTA), the CD spectra were completely altered and did not exhibit a classical α-helix curve.

Figure 5A:
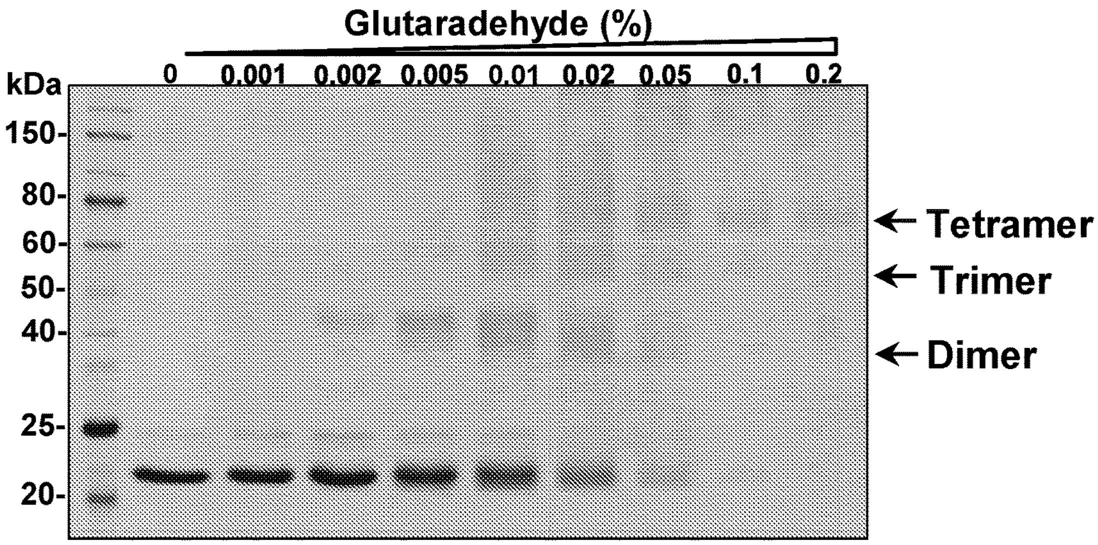

FIG. 5A: Glutaraldehyde cross-linking of rM2-1. 1.2 μg of rM2-1 protein was incubated with increasing amounts of glutaraldehyde from 0-2% at 25° C. for 30 s. The reaction was stopped by adding Tris-HCl (pH7.4) at a final concentration of 50 mM. The cross-linked products were analyzed by 12% SDS-PAGE gel, followed by Coomassie blue staining. The predicted dimer, trimer, and tetramer are indicated.

Figure 5B:
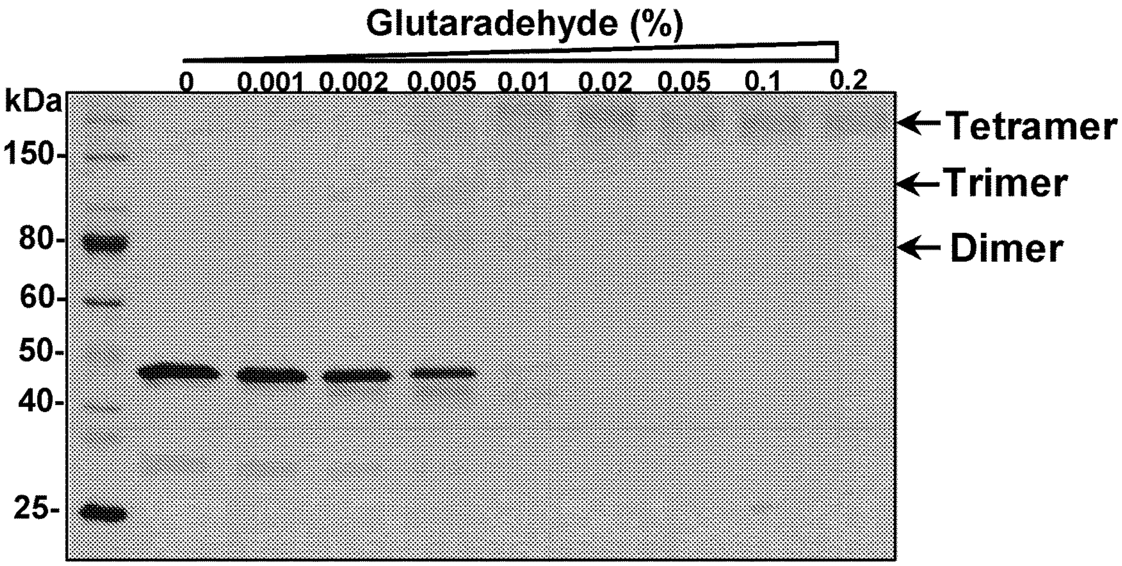

FIG. 5B: Glutaraldehyde cross-linking of GST-M2-1.

Figure 5C:
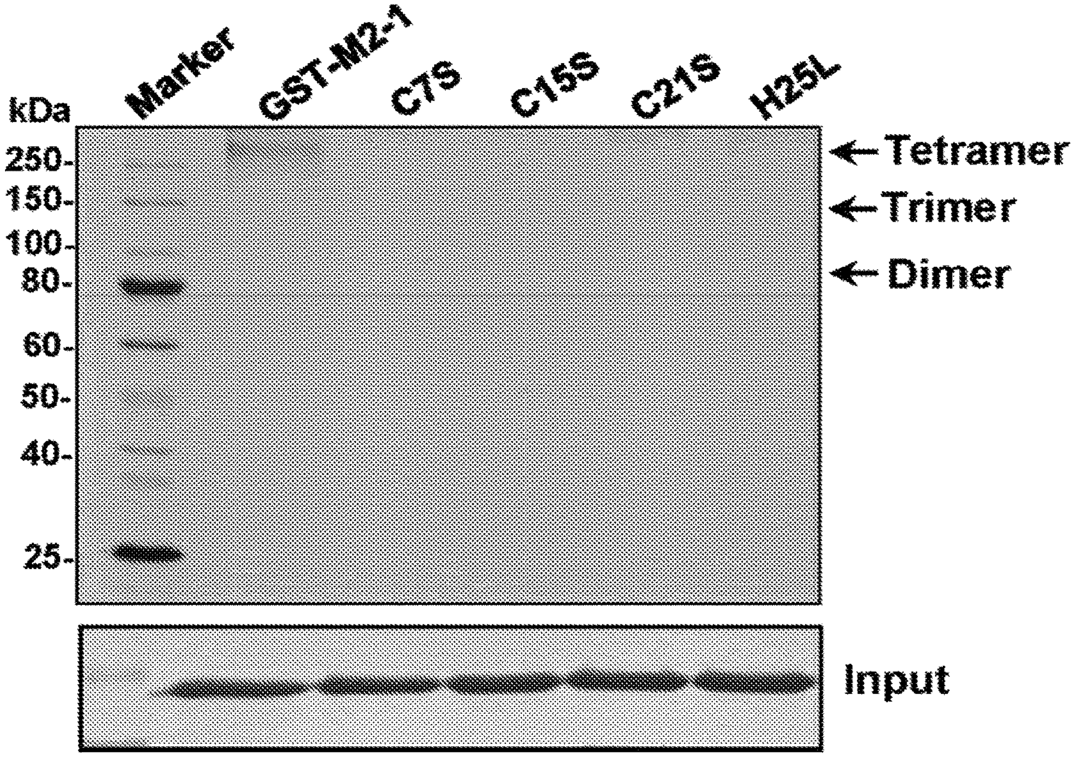

FIG. 5C: Glutaraldehyde cross-linking of GST-M2-1 mutants. 1.2 μg of each GST-M2-1 mutant was incubated with 2% glutaraldehyde, and the products were analyzed by SDS-PAGE.

Figure 6:
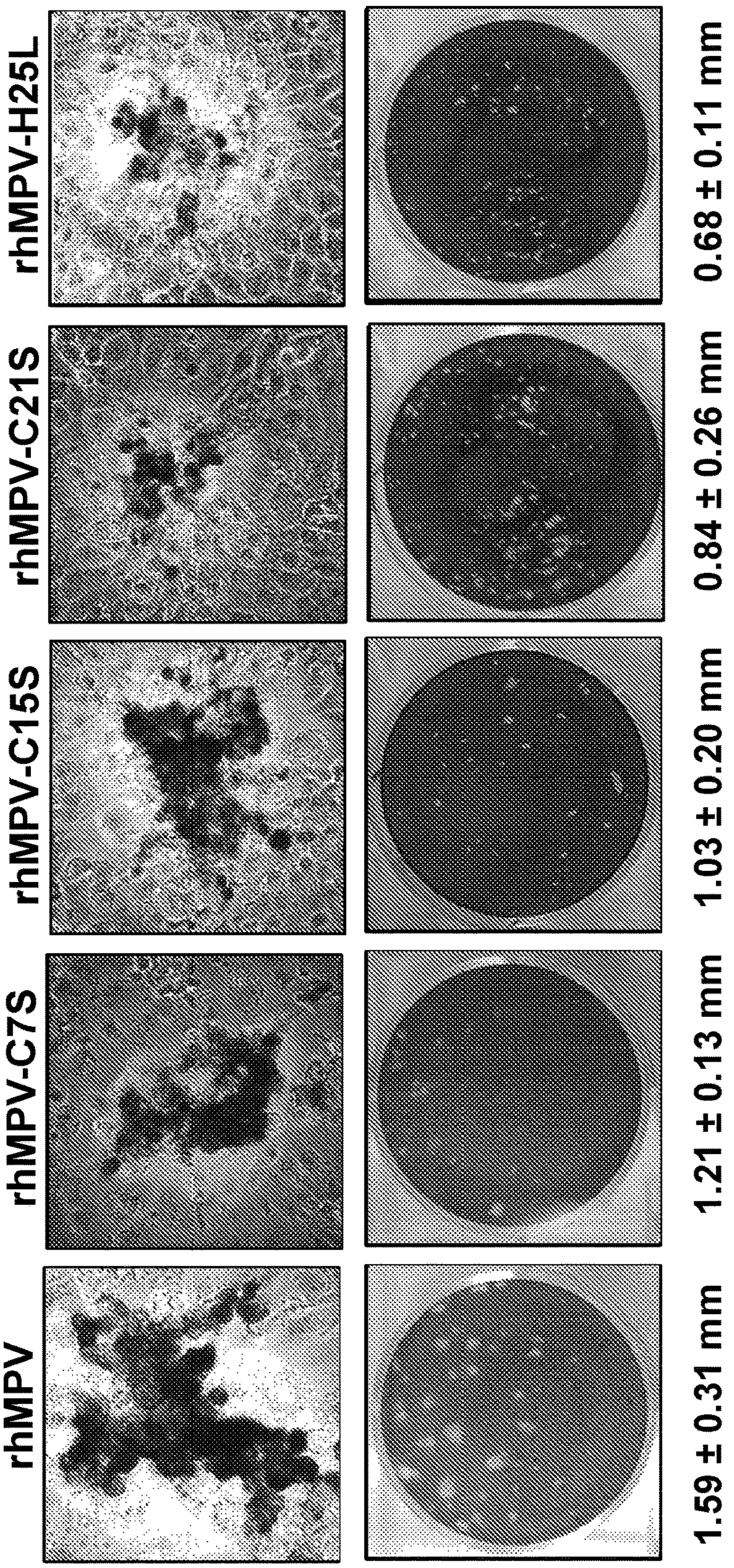

FIG. 6: Recovery of recombinant hMPVs carrying mutations in the zinc binding motif. Top panels: Immunostaining spots formed by recombinant hMPVs. LLC-MK2 cells were infected with recombinant hMPV mutants and incubated at 37° C. for 1 h. At day 4 post-infection, the cells were stained with an anti-hMPV N protein monoclonal antibody. Bottom panels: Plaque morphology of recombinant hMPVs. An agarose overlay plaque assay was performed in monolayer LLC-MK2 cells. Viral plaques were developed at day 6 post-infection.

Figure 7:
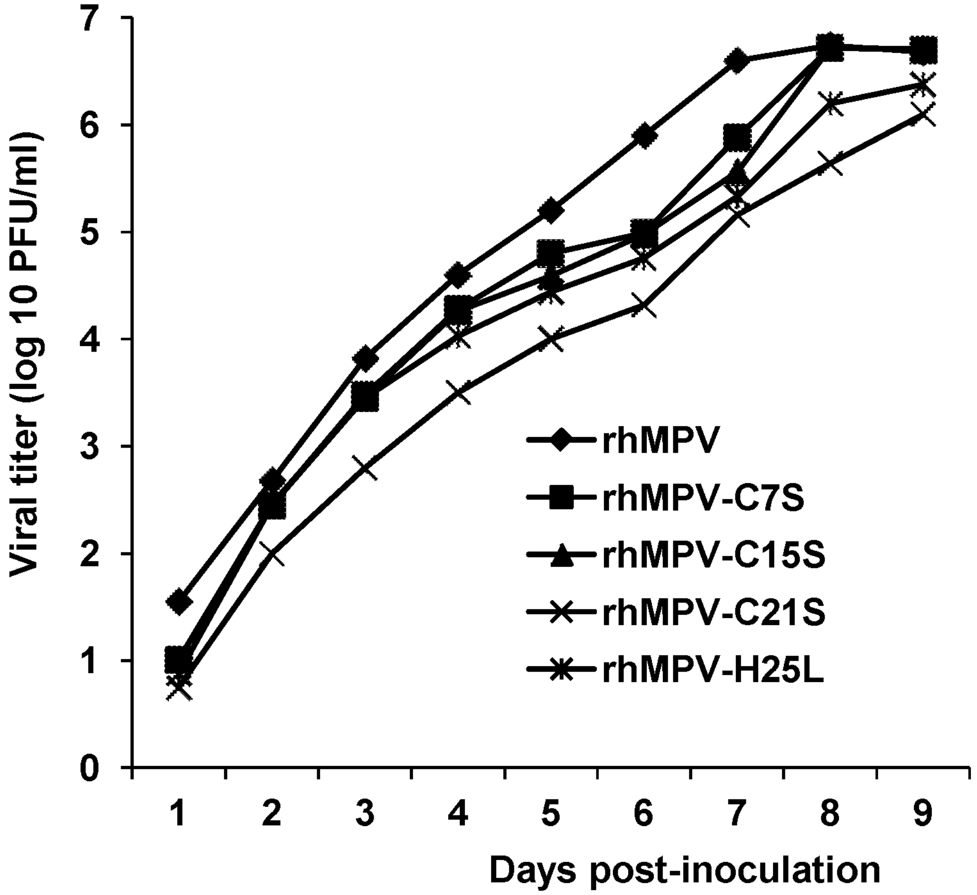

FIG. 7: Single step growth curve of recombinant hMPVs carrying mutations in the zinc binding site. Vero E6 cells in 35-mm dishes were infected with each recombinant hMPV at MOI=0.01. After adsorption for 1 h, the inoculums were removed and the infected cells were washed 3 times with OPTI-MEM. Then, fresh OPTI-MEM containing 2% FBS was added and cells were incubated at 37° C. for various time periods. Aliquots of the cell culture fluid were removed at the indicated intervals. Viral titer was determined by an immunostaining assay in Vero-E6 cells.

Figure 8:
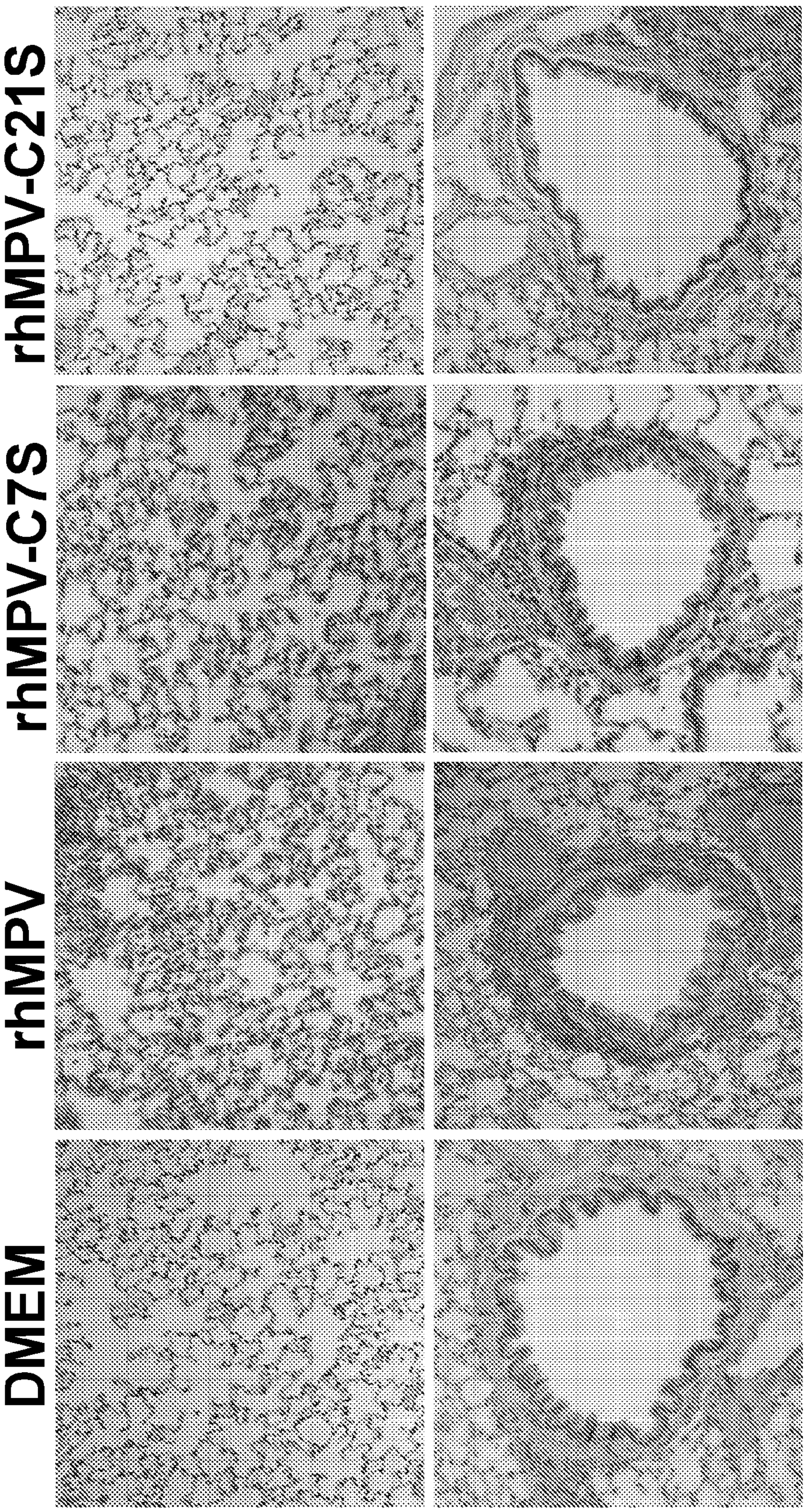

FIG. 8: Lung histological changes in cotton rats infected by rhMPVs. Right lung from each cotton rat was preserved in 4% (v/v) phosphate-buffered paraformaldehyde. Fixed tissues were embedded in paraffin, sectioned at 5 microns, and stained with hematoxylin-eosin (HE) for the examination of histological changes by light microscopy.

Figure 9:
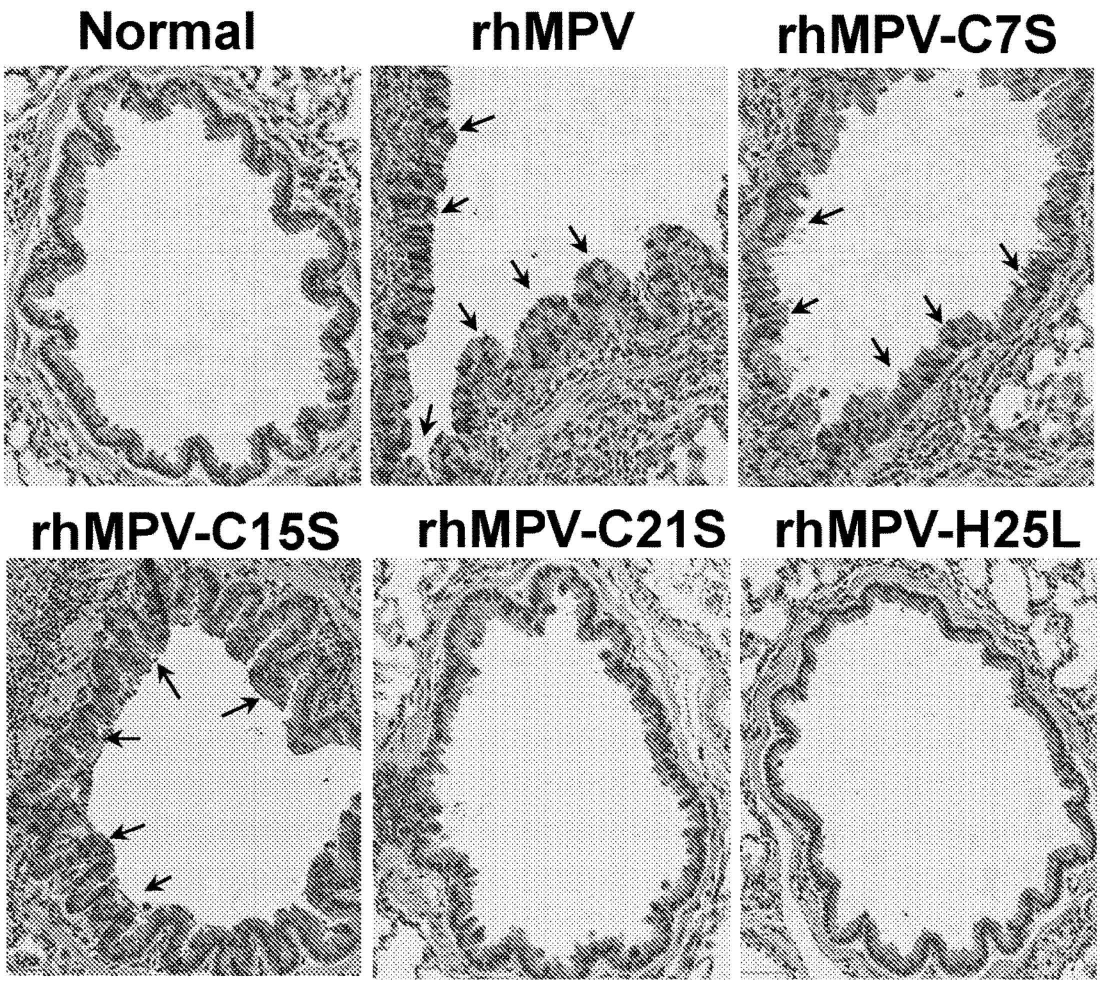

FIG. 9: Immunohistochemical (IHC) staining of lungs from cotton rats infected by rhMPVs. Lung tissues were fixed in 4% (v/v) phosphate-buffered paraformaldehyde. Deparaffinized sections were stained with monoclonal antibody against hMPV matrix protein (Virostat, Portland, ME) to determine the distribution of viral antigen (indicated by arrows).

Figure 10:
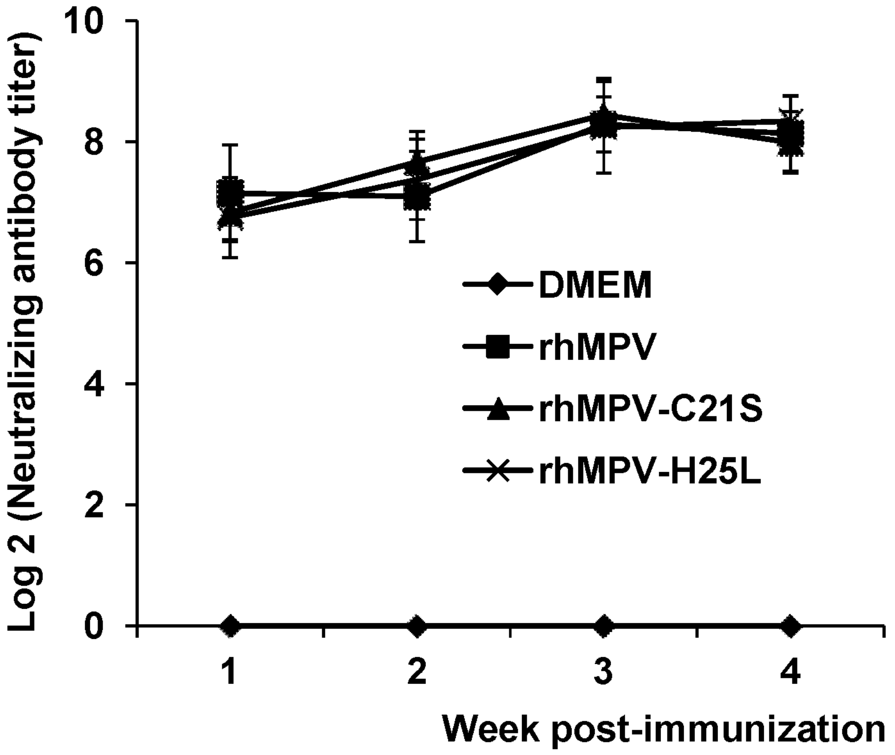

FIG. 10: Recombinant hMPVs triggered a high level of neutralizing antibody in cotton rats. Cotton rats were immunized by one of rhMPV, rhMPV-C21S, or rhMPV-H25L intranasally at a dose of $1.0\times10^6$ PFU per rat (DMEM uninfected control). Blood samples were collected from each rat weekly by retro-orbital bleeding. The hMPV neutralizing antibody was determined using the plaque reduction neutralization assay described herein (see Examples).

Figure 11:
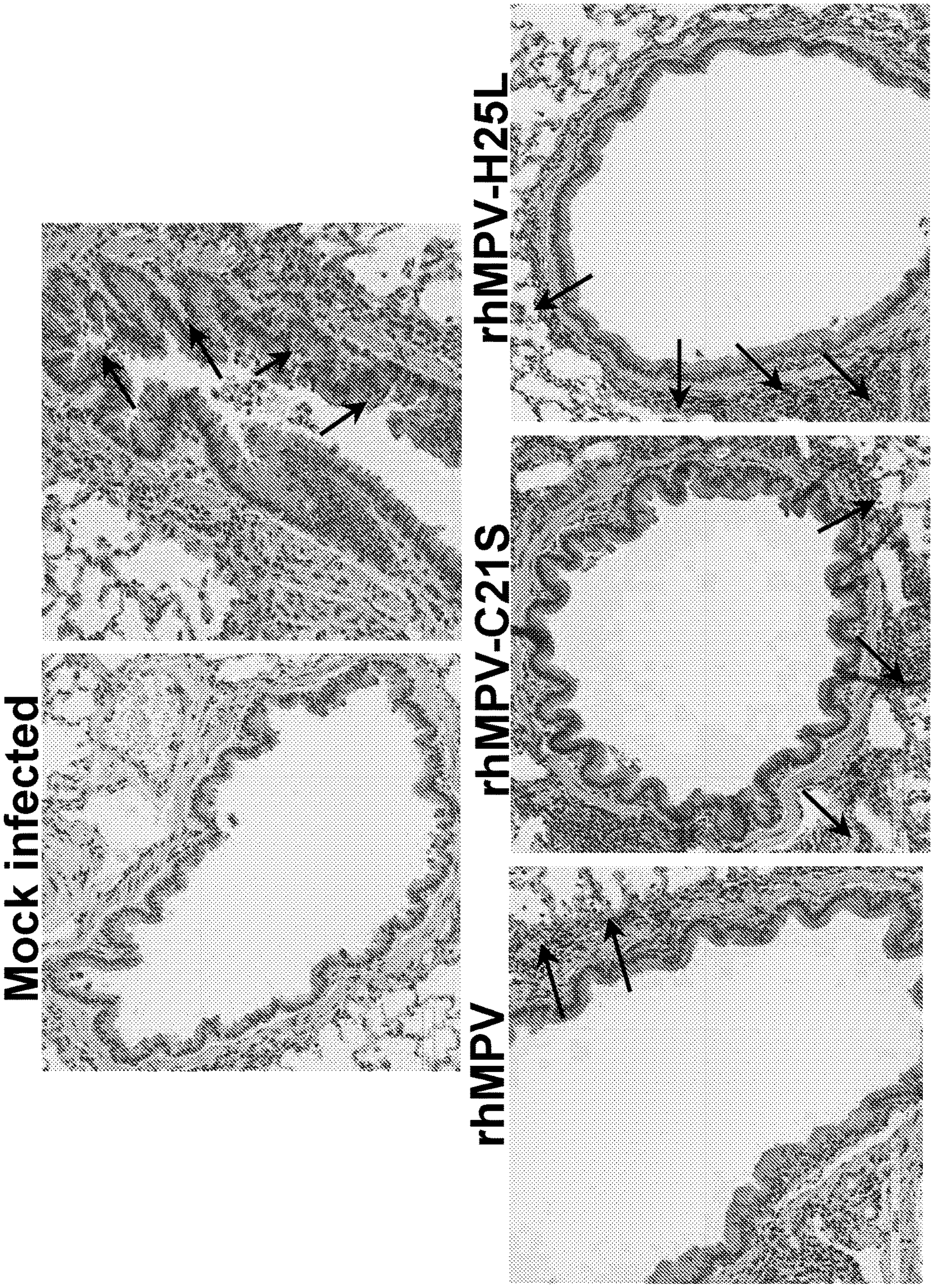

FIG. 11: Immunohistochemical (IHC) staining of lungs from cotton rats vaccinated by rhMPV mutants followed by rhMPV challenge. Lung tissues were fixed in 4% (v/v) phosphate-buffered paraformaldehyde. Deparaffinized sections were stained with monoclonal antibody against hMPV matrix protein (Virostat, Portland, Me.) to determine the distribution of viral antigen. Arrow indicates antigen positive cells.

Figure 12:
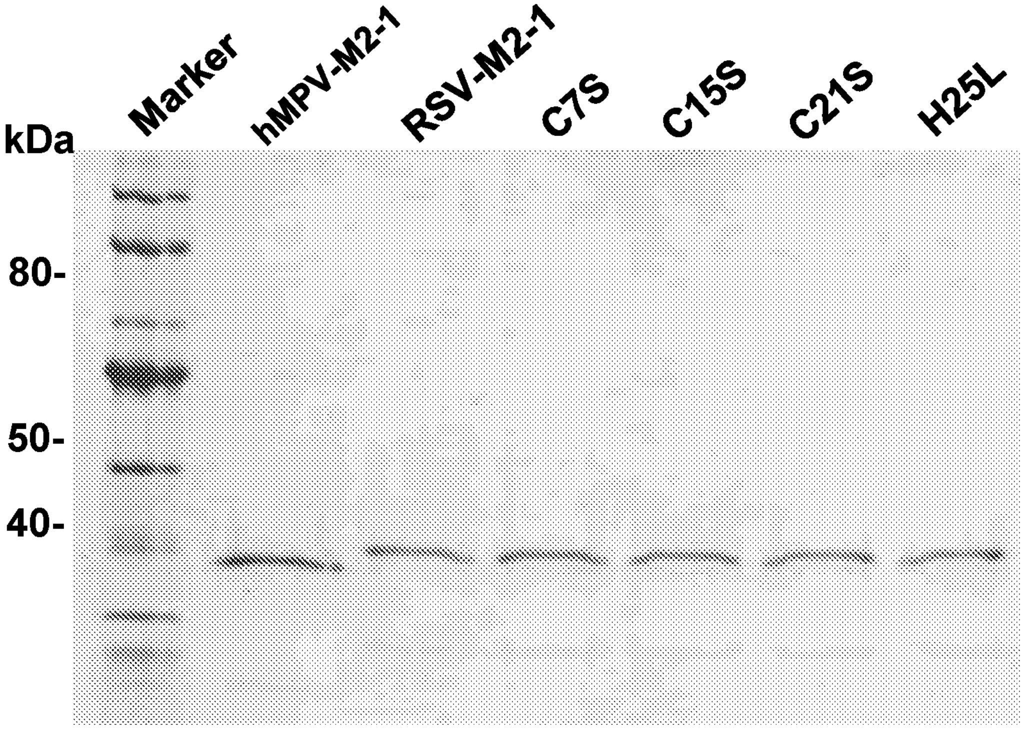

FIG. 12: Expression and purification of RSV M2-1 wild-type and mutant protein.

Figure 13:
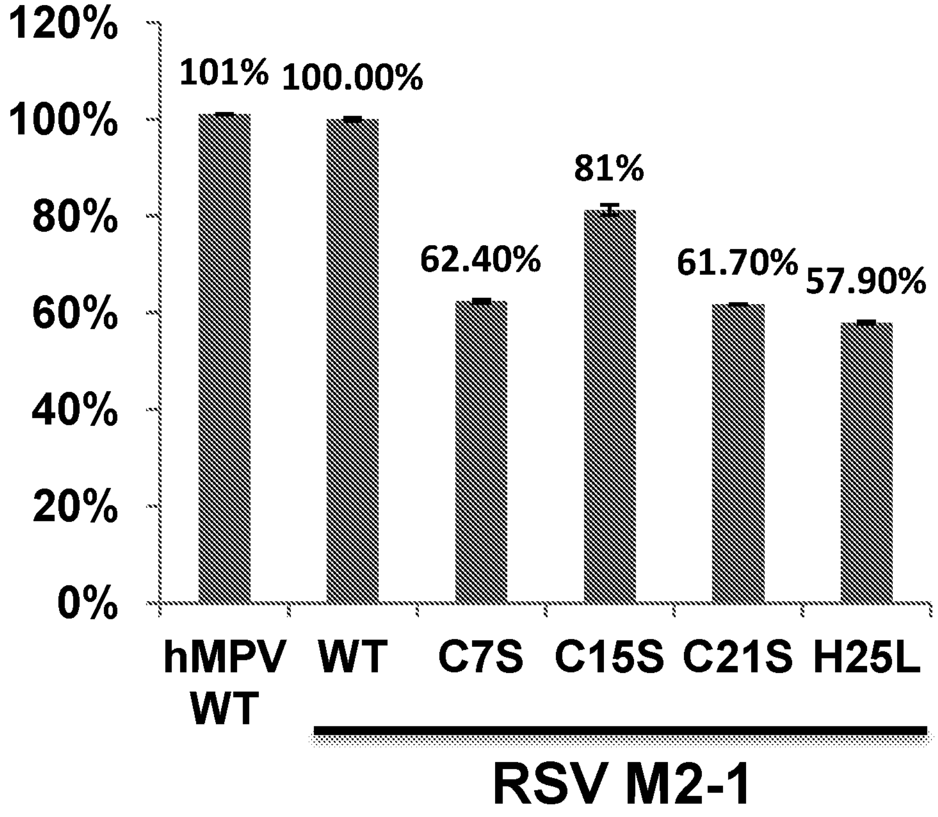

FIG. 13: Mutations in RSV M2-1 protein diminish zinc binding activity.

Figure 14:
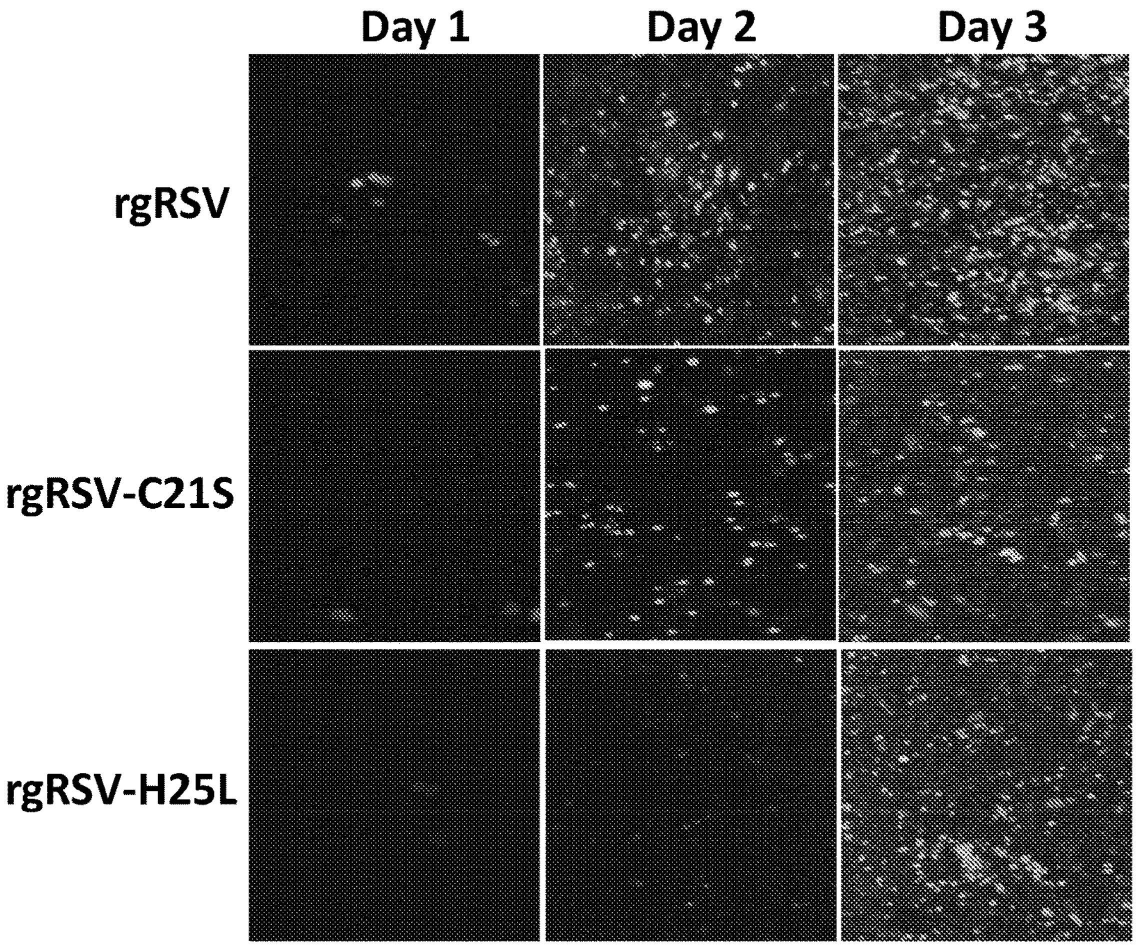

FIG. 14: Recombinant RSV carrying mutations in M2-1 protein had delayed viral replication in cell culture.

BRIEF DESCRIPTION OF THE SEQUENCE LISTING

SEQ ID NO: 1 discloses the amino acid sequence of human metapneumovirus subtype A (hMPV-A; gi: 215794520).

SEQ ID NO: 2 discloses the amino acid sequence of human metapneumovirus subtype B (hMPV-B; gi: 215794505).

SEQ ID NO: 3 discloses the amino acid sequence of avian metapneumovirus subtype A (aMPV-A; gi: 49823139).

SEQ ID NO: 4 discloses the amino acid sequence of avian metapneumovirus subtype B (aMPV-B; gi: 310772463).

SEQ ID NO: 5 discloses the amino acid sequence of avian metapneumovirus subtype C (aMPV-C; gi: 237847064).

SEQ ID NO: 6 discloses the amino acid sequence of human respiratory syncytial virus type A (hRSV-A; gi: 333959).

SEQ ID NO: 7 discloses the amino acid sequence of human respiratory syncytial virus type B (hRSV-B; gi: 2582031).

SEQ ID NO: 8 discloses the amino acid sequence of bovine respiratory syncytial virus (BRSV; gi: 210823).

SEQ ID NO: 9 discloses the amino acid sequence of pneumonia virus of mice (PVM; gi: 56900724).

DETAILED DESCRIPTION

Throughout this disclosure, various publications, patents and published patent specifications are referenced. The disclosures of these publications, patents and published patent specifications are hereby incorporated by reference into the present disclosure to more fully describe the state of the art to which this invention pertains.

In particular embodiments described herein are mutated pneumoviruses, wherein the pneumovirus is mutated relative to a comparable wild-type pneumovirus. In certain embodiments, the mutated pneumovirus is recoverable. The mutated pneumovirus can be any pneumovirus comprising a CCCH zinc binding motif, including but not limited to human metapneumovirus subtype A (hMPV-A), human metapneumovirus subtype B (hMPV-B), avian metapneumovirus subtype A (aMPV-A), avian metapneumovirus subtype B (aMPV-B), avian metapneumovirus subtype C (aMPV-C), avian metapneumovirus subtype D (aMPV-D), human respiratory syncytial virus type A (hRSV-A), human respiratory syncytial virus type B (hRSV-B), bovine respiratory syncytial virus (BRSV), and pneumonia virus of mice (PVM). In certain embodiments, the mutated pneumovirus is a mutated hMPV, a mutated hRSV, or a mutated aMPV.

The recoverable mutated pneumovirus is attenuated in vivo. The mutated pneumovirus, or an immunogenic part thereof, can be used as a pneumovirus vaccine. Vaccines described herein can be utilized to induce a protective immune response in a subject against future viral challenge.

General Description

Using highly purified human metapneumovirus (hMPV) M2-1 protein expressed from *E.coli*, the studies described herein showed that hMPV M2-1 is a zinc binding protein that coordinates zinc ions at a molecular ratio of 1:1. Subsequent mutagenesis showed that C21 and H25 in the zinc binding motif are essential for efficient zinc binding activity, whereas C7 and C15 play more minor roles in zinc binding. Recombinant hMPVs (rhMPVs) lacking zinc binding activity were not only highly attenuated in replication in cell culture and in cotton rats, but also elicited high level of neutralizing antibody and provided protection against viral challenge by rhMPV. In contrast, rhMPV mutants retaining approximately 60% of zinc binding activity replicated as efficiently as wild-type (wt) rhMPV in vitro and in vivo. Collectively, these data indicate that the zinc binding activity of M2-1 is indispensable for hMPV viral replication and pathogenesis in vivo.

The studies described herein further showed that hRSV M2-1 binds and coordinates zinc ion through a CCCH motif at a molecular ratio of 1:1, similarly to the hMPV M2-1 protein. Mutagenesis showed that mutations at C7, C21, and H25 decreased hRSV M2-1 zinc binding by approximately 40%, while a mutation at C15 decreased zinc binding by approximately 20%. Unlike in previous studies where amino acid substitutions (C to G) in the first three cysteine residues (C7, C15, and C21) were lethal to RSV (Tang R S et al., 2001. *Requirement of cysteines and length of the human respiratory syncytial virus M2-1 protein function and virus availability.* J. Virol. 75:11328-35), the C7S, C15S, C21S, and H25L hRSV M2-1 mutants described herein were all recoverable. Furthermore, the C21S and H25L mutants described herein were shown to be attenuated in vitro.

Figure 1:
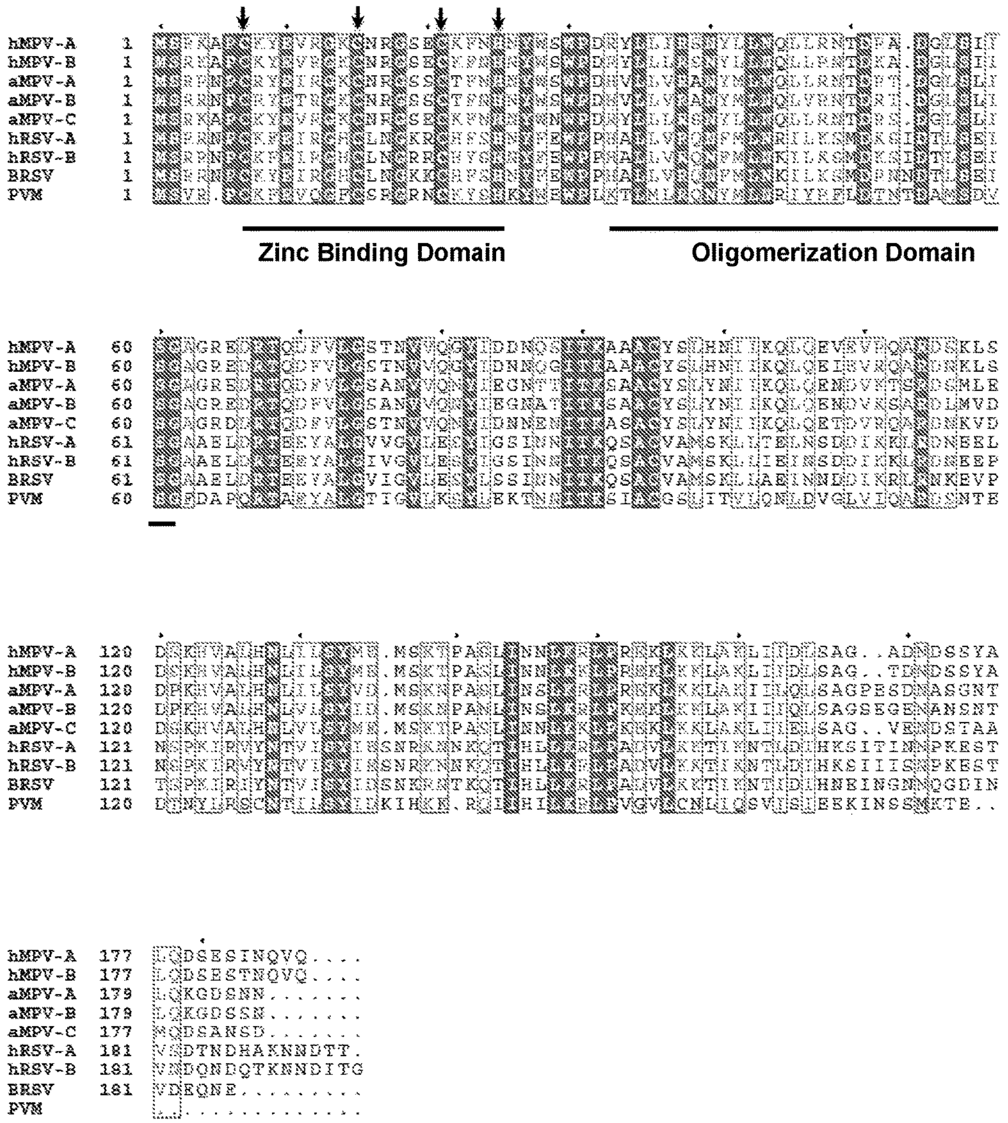
FIG. 1: Sequence alignment of pneumovirus M2-1 proteins. Representative pneumoviruses include: human metapneumovirus subtype A (hMPV-A; gi: 215794520; SEQ ID NO: 1); human metapneumovirus subtype B (hMPV-B; gi: 215794505; SEQ ID NO: 2); avian metapneumovirus subtype A (aMPV-A; gi: 49823139; SEQ ID NO: 3); avian metapneumovirus subtype B (aMPV-B; gi: 310772463; SEQ ID NO: 4); avian metapneumovirus subtype C (aMPV-C; gi: 237847064; SEQ ID NO: 5); human respiratory syncytial virus type A (hRSV-A; gi: 333959; SEQ ID NO: 6); human respiratory syncytial virus type B (hRSV-B; gi: 2582031; SEQ ID NO: 7); bovine respiratory syncytial virus (BRSV; gi: 210823; SEQ ID NO: 8); and pneumonia virus of mice (PVM; gi: 56900724; SEQ ID NO: 9). Fully conserved residues are highlighted by red box, conserved substitutions are indicated by red letters, and black letters mean no match. The zinc binding domain (aa: 7-31) and oligomerization domain (aa: 32-53) are indicated by underline. Zinc binding motif (CCCH) is indicated by arrows.

As shown in FIG. 1, all pneumoviruses have a conserved CCCH zinc binding motif in the M2-1 protein. A recombinant pneumovirus comprises a nucleotide sequence capable of encoding a pneumovirus having a mutated zinc binding domain in the M2-1 protein of the pneumovirus. The CCCH zinc binding motif can be mutated at one or more amino acids. In certain embodiments, the one or more mutations are not lethal to the pneumovirus. In certain embodiments, the CCCH biding motif is mutated at a single amino acid. For example, any one of the cysteine residues of the zinc binding motif (C7, C15, C21, and H25) can be mutated to serine, while the histidine residue can be mutated to leucine. It will be recognized that the CCCH residues can be mutated to any other amino acid that results in a recoverable pneumovirus (i.e., a non-lethal mutation).

Figure 2A:
FIG. 2A hRSV M2-1 tetramer. Structure was generated using PDB ID:4C3D.
Figure 2B:
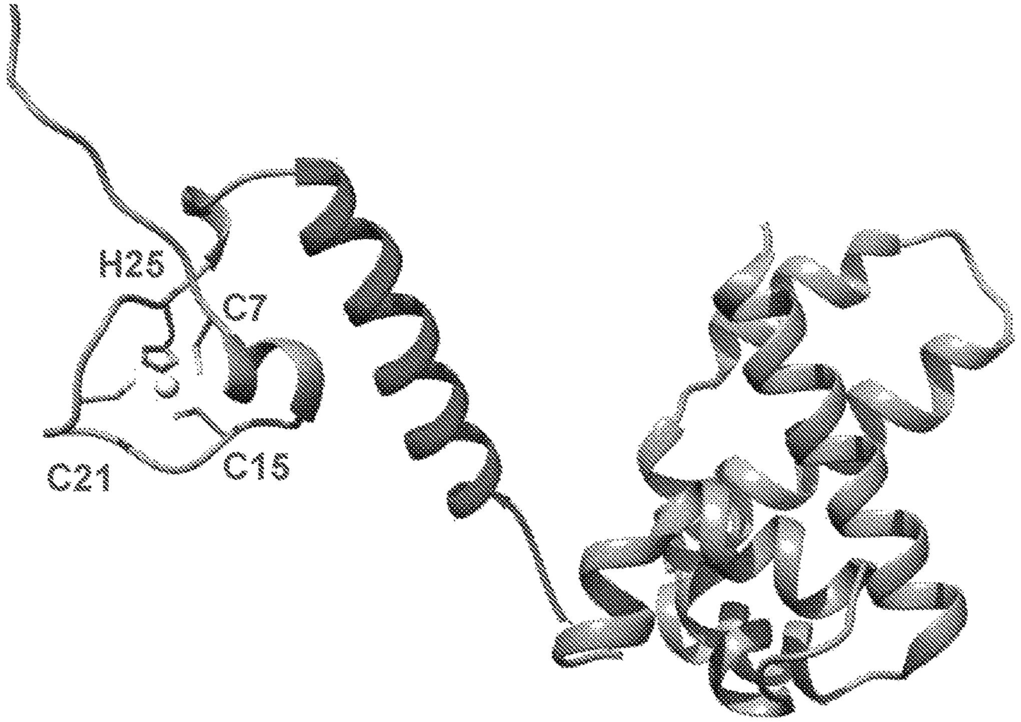
FIG. 2B: hRSV M2-1 monomer. Oligomerization domain is highlighted in red.
Figure 2C:
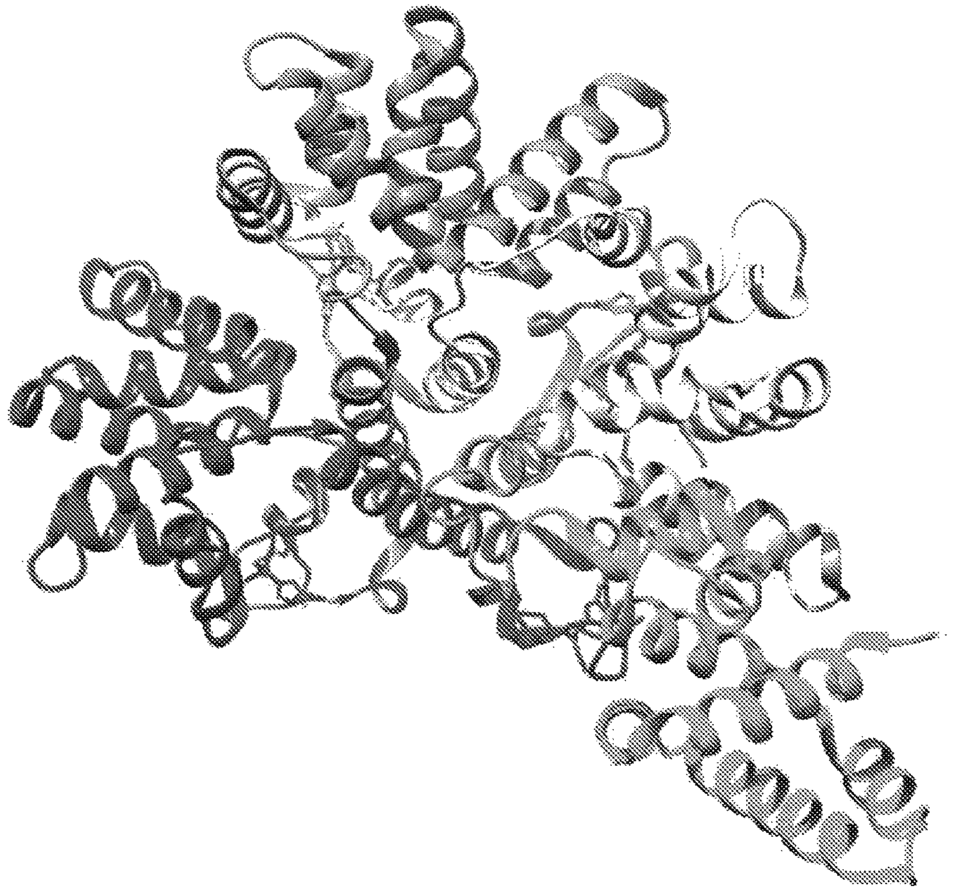
FIG. 2C: hMPV M2-1 tetramer. Structure was generated using PDB ID: 4CS7.
Figure 2D:
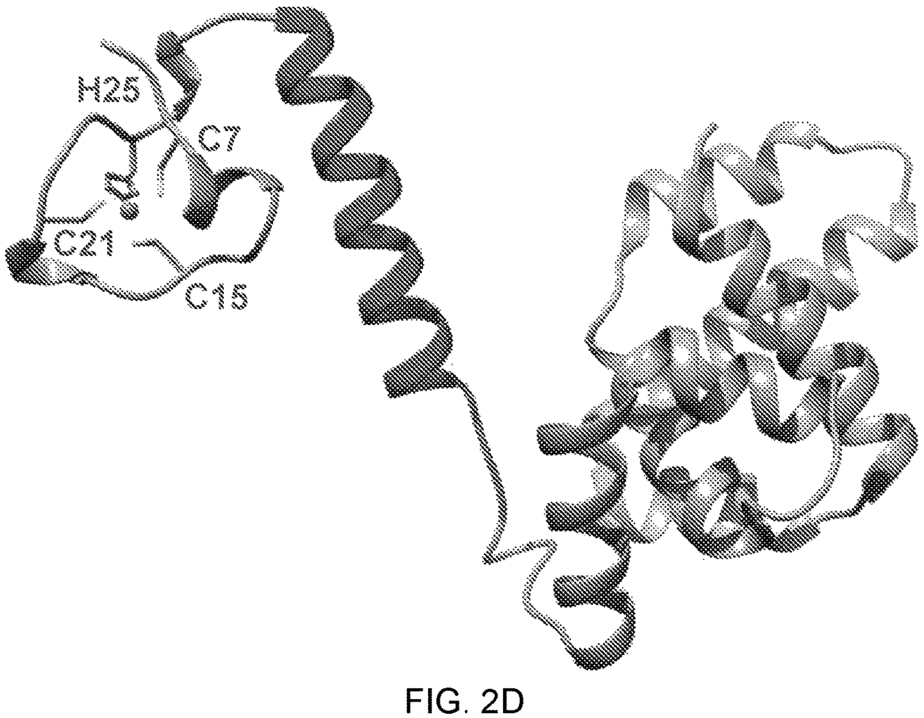
FIG. 2D: hMPV M2-1 monomer. The predicted oligomerization domain is highlighted in red.

Recently, the crystal structures of both the hRSV and hMPV M2-1 proteins were solved (Tanner S J et al., 2014. *Crystal structure of the essential transcription antiterminator M2-1 protein of human respiratory syncytial virus and implications of its phosphorylation.* PNAS USA, 111:1580-85) (see FIGS. 2A-2D). The M2-1 protein of hRSV forms a disk-like symmetrical tetramer, which is driven by a long helix forming a four-helix bundle at its center, and stabilized by contact between the zinc-binding domain and adjacent protomers (FIG. 2A). Each M2-1 monomer forms three distinct regions including a zinc binding domain, tetramerization helix, and a core domain, which are linked by unstructured or flexible sequences (FIG. 2B). In contrast to the hRSV M2-1 structure, the hMPV M2-1 protein forms an asymmetric tetramer, in which three of the protomers exhibit a closed conformation and one forms an open conformation (FIG. 2C). Each protomer is composed of an N-terminal zinc finger domain and an α-helical tetramerization motif forming a rigid unit, followed by a flexible linker and an α-helical core domain (FIG. 2D). Despite these significant discoveries, the biological roles of the zinc binding motif in maintenance of M2-1 functions, viral replication, and pathogenesis in vivo are still poorly understood.

As described in the Examples below, the last two amino acid residues in the zinc binding motif in hMPV M2-1 (C21 and H25) are essential for zinc binding activity and that the amino acids in the zinc binding motif are essential for oligomerization of M2-1 protein. Unlike reports for RSV, rhMPVs lacking zinc binding activity were successfully recovered from infectious cDNA clones. rhMPVs lacking zinc binding activity were not only attenuated in vitro cell culture system, but also attenuated in viral replication in upper and lower respiratory tract of cotton rats. Unlike rhMPV lacking the entire M2-1 gene, cotton rats immunized with rhMPVs lacking zinc binding activity triggered a high level of neutralizing antibody and were completely protected from viral challenge with wild-type rhMPV.

Also described in the Examples below, and contrary to previous reports, is the recoverability of rhRSV comprising single amino acid mutations in the zinc binding motif. Whereas it was previously reported that single amino acid substitutions in the first three cysteine residues (namely C7G, C15G, and C21G) were lethal to hRSV thus preventing recovery of the virus (Tang R S et al., 2001. *Requirement of cysteines and length of the human respiratory syncytial virus M2-1 protein function and virus availability.* J. Virol. 75:11328-35), recombinant RSV-GFP (rgRSV) comprising a single amino acid mutation in the zinc binding motif (C7S, C15S, C21S, or H25L) was recoverable. Additionally, rgRSV-C21S and H25L were attenuated in vitro. In certain embodiments, an attenuated recombinant pneumovirus with at least one amino acid mutation at C7, C15, C21 or H25 is provided. In one particular embodiment, the at least one amino acid mutation is any amino acid mutation that attenuates the pneumovirus and allows for recovery of the recombinant pneumovirus. In another particular embodiment, the at least one amino acid is at least one of C7S, C15S, C21S, and H25L. In yet another particular embodiment, the at least one amino acid mutation is not C7G, C15G, or C21G.

Techniques for introducing mutations into nucleic acids encoding, for example, the pneumovirus M2-1 protein, are well-known to the skilled person and include, for example, but without limitation site-directed mutagenesis by PCR, homologous recombination, restriction enzyme digestion, ligation, CRISPR/Cas-9 etc. Standard reference works setting forth the general principles of recombinant DNA technology include *Molecular Cloning: A Laboratory Manual,* 2nd ed., vol. 1-3, ed. Sambrook et al., Cold Spring Harbor Laboratory Press, Cold Spring Harbor, N.Y., 1989; *Current Protocols in Molecular Biology,* ed. Ausubel et al., Greene Publishing and Wiley-Interscience, New York, 1992 (with periodic updates); Innis et al., *PCR Protocols: A Guide to Methods and Applications,* Academic Press: San Diego, 1990. For further description of CRISPR/Cas-9, see US20100076057A1, WO2010075424A2, WO2013126794A1, WO2013142578, WO2013169398, WO2013176772A1, US2013181440A1, US20140017214A1, WO2014011237A1, WO2014022702A2, WO2014071219A1, U.S. Pat. No. 8,697,359B1, and WO2014018423A2.

In certain embodiments wherein the recombinant pneumovirus is either a metapneumovirus or a respiratory syncytial virus, a virus comprising a mutated zinc binding domain in the M2-1 protein resulting in partially inhibited zinc binding activity will be recoverable. In other embodiments wherein the recombinant pneumovirus is a metapneumovirus, a virus comprising mutated zinc binding domain in the M2-1 protein resulting in abolished zinc binding activity will be recoverable. For metapneumoviruses, the amino acids of the CCCH binding motif can be substituted by any other amino acid that results in partially inhibited or abolished zinc binding activity. For respiratory syncytial virus, a moderate substitution, such as cysteine to serine (differs at a single atom—the sulfur of cysteine thiol is replaced by the serine oxygen in an alcohol), will partially inhibit the zinc binding activity of the M2-1 protein, resulting in an attenuated but recoverable virus. Other possible substitutions for cysteine residues of the CCCH zinc binding domain of a respiratory syncytial virus M2-1 protein include alanine, threonine, and methionine, while the histidine residue can be substituted by leucine, lysine, arginine, valine, isoleucine, methionine, or proline, as well as others.

In certain embodiments where the pneumovirus is a human metapneumovirus, the pneumovirus comprises a nucleotide sequence encoding a zinc binding domain in the M2-1 protein wherein C21 is mutated, for example, to serine (C21S). In other embodiments, the nucleotide sequence encodes a zinc binding domain in the M2-1 wherein H25 is mutated, for example, to leucine (H25L). Where the M2-1 protien comprises two or more mutated amino acids, at least one of the mutations is a mutation of either C21 or of H25. Additional mutations can include mutations to one or both of C7 and C15. In particular embodiments, cysteine residues are mutated to serine residues and histidine is mutated to leucine, however, as described above any non-lethal mutation can be used.

Where the pneumovirus is an avian metapneumovirus, the pneumovirus comprises a nucleotide sequence encoding a zinc binding domain in the M2-1 protein wherein C21 is mutated, for example, to serine (C21S). In other embodiments, the nucleotide sequence encodes a zinc binding domain in the M2-1 wherein H25 is mutated, for example, to leucine (H25L). Where the M2-1 protein comprises two or more mutated amino acids, at least one of the mutations is a mutation of either C21 or of H25. Additional mutations can include mutations to one or both of C7 and C15. In particular embodiments, cysteine residues are mutated to serine residues and histidine is mutated to leucine, however, as described above any non-lethal mutation can be used.

In embodiments where the pneumovirus is a human respiratory syncytial virus, the pneumovirus comprises a nucleotide sequence encoding a zinc binding domain in the M2-1 protein wherein C21 is mutated, for example, to serine (C21S). In other embodiments, the nucleotide sequence encodes a zinc binding domain in the M2-1 wherein H25 is mutated, for example, to leucine (H25L). Where the M2-1 protein comprises two or more mutated amino acids, at least one of the mutations is a mutation of either C21 or of H25. Additional mutations can include mutations to one or both of C7 and C15. In particular embodiments, cysteine residues are mutated to serine residues and histidine is mutated to leucine, however, any non-lethal mutation can be used.

Any mutated pneumovirus described herein can be used in a vaccine to induce a protective immune response in a subject. A mutated pneumovirus is generally used in a vaccine for a wild-type pneumovirus of the same type. For example, a mutated human metapneumovirus can be used as a vaccine in a human subject, where administration of the vaccine comprising the mutated human metapneumovirus to the subject induces a protective immune response in the subject, thereby protecting the subject from future viral challenge by wild-type human metapneumovirus. In certain embodiments, the vaccine is a live attenuated vaccine.

Subjects that may benefit from a vaccine described herein include but are not limited to humans, fowl, including but not limited to turkey (*Meleagris* spp.), chicken (*Gallus* spp.), pheasant (*Phasianus* spp.), Muscovy duck (*Cairina moschata*), and guinea fowl (family Numididae), cattle, and rodents.

Vaccines of the present invention comprise a mutated pneumovirus described herein, or an immunogenic part thereof, in an amount or concentration sufficient to induce a protective immune response in a subject (i.e, an immunologically effective dose). It will be known to one of skill in the art how to determine the amount or concentration required to induce a protective immune response in the subject. In certain embodiments, an immunologically effective dose can be from about $10^3$ PFU/kg to about $10^7$ PFU/kg, or any range or value therein. In other embodiments the effective dose can be from about $10^5$ PFU/kg to about $10^6$ PFU/kg.

In certain embodiments, the mutated pneumovirus or an immunogenic part thereof is present in a vaccine composition. The vaccine composition, in addition to the mutated pneumovirus or immunogenic part thereof, may further comprise a pharmaceutically acceptable carrier, vehicle, excipient, or combination thereof, thereby forming a pharmaceutical vaccine composition. A vaccine composition can also comprise one or more adjuvants. Pharmaceutically acceptable carriers, vehicles, excipients, and adjuvants are generally well understood in the art, as is preparation of vaccines, including live attenuated vaccines.

Vaccine compositions can be administered to a subject by any known means for vaccine administration. Administration routes can include, but are not limited to intranasal administration, subcutaneous administration, intramuscular administration, intradermal administration, and oral administration. One of skill in the art will readily be able to identify an appropriate means for administering a vaccine, live attenuated vaccine, or vaccine composition described herein to a particular subject.

In certain embodiments, subjects are administered two or more doses of a vaccine described herein. A second dose of a vaccine can be administered at any interval following the initial dose. Following initial immunization, where a protective immune response is induced in a subject, additional doses of the same vaccine can prevent decreases in circulating neutralizing antibody levels, thereby prolonging the protective immune response. In certain embodiments, the interval between first and second immunizations is approximately one week, approximately, two weeks, approximately three weeks, approximately four weeks, approximately five weeks, approximately six weeks, approximately seven weeks, and approximately eight weeks. Alternatively, levels of neutralizing antibody in a subject can be monitored, with additional immunizations administered when neutralizing antibodies reach levels that no longer confer a protective effect.

Kits

Another embodiment described herein relates to kits for use with the compositions and methods described herein. Certain embodiments include kits having one or more pharmaceutical or vaccine compositions or boost compositions of use to prevent or treat subjects exposed to or having a pathogen or condition. The pathogen can include, but is not limited to, human metapneumovirus subtype A, human metapneumovirus subtype B, avian metapneumovirus subtype A, avian metapneumovirus subtype B, avian metapneumovirus subtype C, avian metapneumovirus subtype D, human respiratory syncytial virus type A, human respiratory syncytial virus type B, bovine respiratory syncytial virus, and pneumonia virus of mice. Kits can be portable, for example, able to be transported and used in remote areas. Other kits may be of use in a health care facility to immunize a subject, or to treat a subject having been exposed to a virus or suspected of having been exposed or at risk of exposure to a virus. Kits can include one or more pharmaceutical compositions and/or vaccine compositions comprising at least one mutant pneumovirus described herein that can be administered before, during, or after exposure to a virus. In other embodiments, kits include dehydrated formulations of pharmaceutical compositions and/or vaccine compositions described herein in order to prolong the half-life of the mutated pneumovirus contained therein (e.g., for stockpiling the pharmaceutical compositions and/or vaccine compositions in the event of an outbreak or providing treatments to remote areas).

Yet other embodiments, kits include a suitable container, such as vials, tubes, mini- or microfuge tubes, test tube, flask, bottle, syringe, or other suitable container. Where an additional component or agent is provided, the kit can contain one or more additional containers into which this agent or component can be placed. Kits herein will also typically include a means for containing the agent, composition and any other reagent containers in close confinement for commercial sale. Such containers can include plastic containers into which the desired vials are placed to be retained. Optionally, one or more additional agents such as other anti-viral agents, anti-fungal or anti-bacterial agents may be needed for compositions described, for example, for pharmaceutical compositions for use as a vaccine.

Definitions

The term "recombinant" is generally used to indicate that the material (e.g., a virus, a nucleic acid, a genetic construct or a protein) has been altered by technical means (i.e., non-naturally) through human intervention. As used herein, the term denotes material (e.g., a virus, a nucleic acid, a genetic construct or a protein) that has been altered by technical means of mutagenesis.

As used herein, the term "antibody" is intended to refer broadly to any immunologic binding agent such as IgG, IgM, IgA, IgD and IgE. "Antibody" may refer to any antibody-like molecule that has an antigen binding region, and includes antibody fragments such as Fab', Fab, F(ab')2, single domain antibodies (DABs), Fv, scFv (single chain Fv), and the like. A "neutralizing antibody" is intended to refer broadly to any antibody which defends a cell from an infectious body, such as a virus, by inhibiting or neutralizing the infectious body's biological activity.

As used herein, "immunogenicity" refers to the ability of a particular substance, such as an attenuated virus, to provoke or initiate an immune response in a subject. Immunogenicity refers to the ability of the substance to induce a humoral and/or cell mediated immune response.

"Composition" refers to any mixture, aqueous or non-aqueous solution, suspension, emulsion, gel, or the like, that contains two or more components. The components can be, for example, an immunostimulatory component that provides an immunostimulatory effect. The immunostimulatory components can be any combination of one or more live attenuated viruses, immunogenic part or parts thereof, one or more adjuvants, or any combination thereof. For example, a composition can comprise two adjuvants so that the composition forms an adjuvant combination. Alternatively, a composition can include an adjuvant and a live attenuated pneumovirus so that the mixture forms, e.g., a vaccine.

As used herein, the term "pharmaceutical composition" encompasses a product comprising one or more active ingredients, and an optional carrier, vehicle, or excipient comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. Generally, pharmaceutical compositions are prepared by uniformly and intimately bringing the active ingredient into association with a liquid carrier, vehicle, or excipient, or a finely divided solid carrier, vehicle, or excipient, or both, and then, if necessary, shaping the product into the desired formulation. The pharmaceutical composition includes enough of the active ingredient to produce the desired effect. Accordingly, the pharmaceutical compositions described herein encompass any composition made by admixing a compound or recombinant pneumovirus mutant of the present invention and a pharmaceutically acceptable carrier, vehicle, or excipient. By "pharmaceutically acceptable" it is meant the carrier, vehicle, or excipient must be compatible with the other ingredients of the formulation and not deleterious to the recipient thereof.

"Vaccine" and "Vaccine Composition" as used herein, refers to a pharmaceutical composition that includes a live attenuated pneumovirus, or an immunogenic part or parts thereof. A vaccine can include components in addition to the live attenuated pneumovirus or immunogenic part or parts thereof, such as, for example, one or more adjuvants, a carrier, etc.

Numbering of amino acids, unless otherwise specified, is of amino acids comprising the pneumovirus M2-1 protein. The first amino acid (from the N-terminus) of M2-1 protein is designated amino acid 1. For example, C21 indicates the presence of cysteine at amino acid position 21 of a pneumovirus M2-1 protein, and the notation C21S indicates the substitution of cysteine at position 21 by serine.

"Immunologically effective dose" as used herein refers to any amount of a vaccine composition that will cause a reduction in one or more of the manifestations of viral challenge, such as viral lesions, viral load, rate of virus production, and mortality as compared to untreated control subjects. It is understood that the immunologically effective dose will be dependent on many factors, including but not limited to the age, sex, health, and weight of the subject. The ranges of immunologically effective doses described herein are not intended to be limiting, and represent possible dose ranges. In certain embodiments, dosage will be tailored to the individual subject. Tailored dosages used during vaccination can also vary depending on the particular nature of the live attenuated vaccine and viral vector used. Determination of dosing requirements is well within the ordinary skill of a physician.

EXAMPLES

The methods and embodiments described herein are further defined in the following Examples. Certain embodiments of the present invention are defined in the Examples herein. It should be understood that these Examples, while indicating certain embodiments of the invention, are given by way of illustration only. From the discussion herein and these Examples, one skilled in the art can ascertain the essential characteristics of this invention and without departing from the spirit and scope thereof, can make various changes and modifications of the invention to adapt it to various usages and conditions.

Example I

Materials and Methods—Human Metapneumovirus

Cell lines. LLC-MK2 (ATCC CCL-7) cells were maintained in Opti-MEM medium (Life Technologies, Bethesda, Md.) supplemented with 2% fetal bovine serum (FBS). Vero E6 cells (ATCC CRL-1586) and BHK-SR19-T7 cells (provided by Apath, LLC, Brooklyn, N.Y.) were grown in Dulbecco's modified Eagle's medium (DMEM; Life Technologies) supplemented with 10% FBS. The medium for the BHK-SR19-T7 cells was supplemented with 10 μg/ml puromycin (Life Technologies) during every other passage to select for T7 polymerase-expressing cells.

Plasmids and site-directed mutagenesis. Plasmids encoding the hMPV minigenome, the full-length genomic cDNA of hMPV strain NL/1/00, and support plasmids expressing hMPV N protein (pCITE-N), P protein (pCITE-P), L protein (pCITE-L), and M2-1 protein (pCITE-M2-1) were provided by Ron A. M. Fouchier at the Department of Virology, Erasmus Medical Center, Rotterdam, The Netherlands. The F cleavage site in the genome of hMPV NL/1/00 was modified to a trypsin-independent F cleavage site. The M2-1 mutants of hMPV were generated by site-directed mutagenesis using the QuikChange methodology (Stratagene, La Jolla, Calif.). All constructs were sequenced at The Ohio State University Plant Microbe Genetics Facility to confirm the presence of the introduced mutations.

Expression and purification of recombinant hMPV M2-1 protein from *E.coli*. The hMPV M2-1 gene was PCR amplified from a cDNA clone of strain NL/1/00 and was inserted into *E. coli* expression system pGEX-4T-1 vector at BamHI and NotI sites. To facilitate the protein purification, the GST protein was fused to the N-terminus of M2-1 gene. The resulting plasmids were transformed into *E. coli* Rosetta (DE3) and grown at 37° C. until the absorbance at 600 nm reached 0.6-0.8. Cells were then chilled on ice for 10 min and protein expression was induced by addition of 20 μM of Isopropyl β-D-1-thiogalactopyranoside (IPTG) and 75 μM of ZnSO4. The cells were grown for an additional 20 h at 25° C. and harvested by centrifugation at 5,000 g for 10 mM. Bacterial pellets were resuspended in lysis buffer (40 mM Tris-HCl (pH 7.4), 1.0 M NaCl, 0.5 mM DTT, and 20 μM ZnSO4) supplemented with 1 mg/ml of lysozyme and protease inhibitor cocktail (Roche, Mannheim, Germany). After 30 min incubation on ice, the cells were lysed using sonication, followed by centrifugation at 15,000 g at 4° C. for 40 min. The supernatant was collected and loaded into a column containing 5 ml of Glutathione HiCap Matrix (Qiagen). The G resins were washed with 150 ml of resuspension buffer, followed by washing with 100 ml of the cleavage buffer (50 mM Tris-HCl (pH 7.6), 2.5 mM CaCl2, 150 mM NaCl, and 0.2 mM DTT). To isolate GST-free M2-1, 20 ml of the cleavage buffer containing 2 units/ml of thrombin (Sigma, St. Louis, Mo.) was loaded into the column and was incubated at room temperature for 8 h. Cleavage was halted by adding APMSF (Sigma).

Similarly, the GST fusion hMPV M2-1 mutants C7S, C15S, C21S and H25L were generated. The purified hMPV M2-1 proteins were dialyzed against PBS buffer containing 300 mM NaCl and 10 μM ZnSO4. Protein concentration was determined by the Bradford assay (Sigma).

Circular Dichroism (CD) spectroscopy. Recombinant hMPV M2-1 protein was dissolved in buffer (40 mM Tris-HCl pH7.4, 10 μM ZnCl2) and dialyzed against this same buffer at 4° C. overnight. 2 μM of M2-1 protein was incubated with increasing concentration of ethylenediaminetetraacetic acid (EDTA), and analyzed by an AVIV far-UV spectropolarimeter at 20° C. using a quartz microcell of 0.1 cm path length with a wavelength range of 190-260 nm at scanning speed of 50 nm per min. Ten individual readings were recorded and averaged. After subtraction of the baseline, the spectra were mathematically transformed into molar ellipticity.

Colorimetric determination of the zinc content. Purified hMPV M2-1 was dialyzed against 50 mM PBS (pH7.0) containing 0.3 M NaCl at 4° C. overnight. M2-1 proteins at concentrations of 2 μM, 3 μM, and 4 μM in 1 ml of solution containing 100 μM 4-(2-Pyridylazo) resorcinol (PAR) were incubated at 25° C. for 20 min and the absorbance at 500 nm was monitored for 5 min. Upon addition of 100 μM p-chloromercuriphenylsulfonic acid (PMPS), the release of strongly bound $Zn^{2+}$ was monitored. The amount of $Zn^{2+}$ bound to hMPV M2-1 was quantified by comparing the sample readings to a standard curve generated using 2 μM, 3 μM, and 4 μM ZnSO4 (Sigma). Buffer containing 50 mM PBS (pH7.0), 0.3M NaCl, and 100 μM PAR was used as the blank control. The $Zn^{2+}$ content of GST-M2-1 and mutants was measured at 2 μM and compared with rM2-1 at the same $Zn^{2+}$ concentration.

Glutaraldehyde cross-linking. 1.2 μg of rM2-1, GST-M2-1 or mutant proteins were diluted in 20 ,d of reaction buffer (50 mM PBS pH7.0, 300 mM NaCl) and were incubated with increasing amounts of glutaraldehyde from 0-2% at 25° C. for 30 sec. The reaction was stopped by the addition of Tris-HCl (pH7.4) at a final concentration of 50 mM. Subsequently, the cross-linked products were analyzed by 12% SDS-PAGE and the proteins were visualized by Coomassie blue staining.

Recovery of rhMPVs from the full-length cDNA clones. RhMPVs were rescued using a reverse genetics system. BHK-SR19-T7 cells (provided by Apath LLC), which stably express T7 RNA polymerase, were transfected with 5.0 μg of plasmid phMPV carrying the full-length hMPV genome, 2.0 μg of pCITE-N, 2.0 μg of pCITE-P, 1.0 μg of pCITE-L, and 1.0 μg of pCITE-M2-1 using Lipofectamine 2000 (Life Technologies). At day 6 posttransfection, the cells were harvested using scrapers and were co-cultured with LLC-MK2 cells at 50-60% confluence. When extensive cytopathic effects (CPE) were observed, the cells were subjected to three freeze-thaw cycles, followed by centrifugation at 3,000×g for 10 min. The supernatant was subsequently used to infect new LLC-MK2 cells. The successful recovery of the rhMPVs was confirmed by immunostaining, agarose overlay plaque assay, and reverse transcription (RT)-PCR.

Immunostaining plaque assay. Vero E6 cells were seeded in 24-well plates and infected with serial dilutions of rhMPV. At day 6 post-infection, the supernatant was removed and cells were fixed in a pre-chilled acetone-methanol solution at room temperature for 15 min. Cells were permeabilized in phosphate-buffered saline (PBS) containing 0.4% Triton X-100 at room temperature for 10 min and blocked at 37° C. for 1 h using 1% bovine serum albumin (BSA) in PBS. The cells were then labeled with an anti-hMPV N-protein primary monoclonal antibody (Millipore, Billerica, Mass.) at a dilution of 1:1,000, followed by incubation with horseradish peroxidase (HRP)-labeled rabbit antimouse secondary antibody (Thermo Scientific, Waltham, Mass.) at a dilution of 1:5,000. After incubation with 3-amino-9-ethylcarbazole (AEC) chromogen substrate (Sigma, St. Louis, Mo.), positive cells were visualized under a microscope. The viral titer was calculated as the number of PFU per ml.

Viral replication kinetics in LLC-MK2 cells. Confluent LLC-MK2 cells in 35-mm dishes were infected with wild-type (wt) rhMPV or mutant rhMPV at an MOI of 0.01. After 1 h of adsorption, the inoculum was removed and the cells were washed three times with PBS. Fresh DMEM (supplemented with 2% FBS) was added and the infected cells were incubated at 37° C. At different time points postinfection, the supernatant and cells were harvested by three freeze-thaw cycles, followed by centrifugation at 1,500×g at room temperature for 15 min. The virus titer was determined by an immunostaining assay in Vero E6 cells.

Replication and pathogenesis of rhMPV in cotton rats. Twenty five 4-week-old female specific-pathogen-free (SPF) cotton rats (Harlan Laboratories, Indianapolis, Ind.) were randomly divided into five groups (5 cotton rats per group). Prior to virus inoculation, the cotton rats were anesthetized with isoflurane. The cotton rats in group 1 were inoculated with $2.0\times10^5$ PFU of wt rhMPV and served as positive controls. The cotton rats in groups 2-5 were inoculated with $2.0\times10^5$ PFU of four rhMPV mutants (rhMPV-C7S, C15S, C21S, and H25L). The cotton rats in group 6 were mock infected with 0.1 ml of Opti-MEM medium and served as uninfected controls. Each cotton rat was inoculated intranasally with a volume of 100 μl. After inoculation, the animals were evaluated on a daily basis for mortality and the presence of any respiratory symptoms. At day 4 postinfection, the cotton rats were sacrificed, and lungs and nasal turbinates were collected for both virus isolation and histological analysis.

Immunogenicity of rhMPVs in cotton rats. Twenty five cotton rats (Harlan Laboratories, Indianapolis, Ind.) were randomly divided into five groups (5 cotton rats per group). The cotton rats in group 1 were mock infected with Opti-MEM medium and used as an infected control, and those in groups 2 to 4 were intranasally inoculated with $2.0\times10^5$ PFU of wt rhMPV, rhMPV-C21S, or H25L in 0.1 ml Opti-MEM medium. The cotton rats in group 5 were inoculated with DMEM and served as the unimmunized challenged control. After immunization, the cotton rats were evaluated daily for mortality and the presence of any symptoms of hMPV infection. Blood samples were collected from each rat weekly by facial vein retro-orbital bleeding, and serum was isolated for neutralizing antibody detection. At week 4 post-immunization, the cotton rats in groups 2 to 5 were challenged intranasally with wild-type rhMPV at a dose of $1.0\times10^6$ PFU per cotton rat.

After challenge, the animals were evaluated twice every day for mortality and the presence of any symptoms of hMPV infection. At day 4 post-challenge, all cotton rats from each group were euthanized by CO2 asphyxiation. The lungs and nasal turbinates from each cotton rat were collected for virus isolation and histological evaluation. The immunogenicity of rhMPV mutants was evaluated using the following methods: (i) humoral immunity was determined by analysis of serum neutralization of virus using an end-point dilution plaque reduction assay; (ii) viral titers in the nasal turbinates and lungs were determined by an immunostaining plaque assay; and, (iii) pulmonary histopathology and viral antigen distribution were determined using the procedure described below. The protection was evaluated with respect to viral replication, antigen distribution, and pulmonary histopathology Pulmonary histology. After sacrifice, the right lung of each animal was removed, inflated, and fixed with 4% neutral buffered formaldehyde. Fixed tissues were embedded in paraffin and sectioned at 5 μm. Slides were then stained with hematoxylin-eosin (H&E) for the examination of histological changes by light microscopy. The pulmonary histopathological changes were reviewed by 2-3 independent pathologists. Histopathological changes were scored to include the extent of inflammation (focal or diffuse), the pattern of inflammation (peribronchiolar, perivascular, interstitial, alveolar), and the nature of the cells making up the infiltrate (neutrophils, eosinophils, lymphocytes, macrophages).

Immunohistochemical (IHC) staining. The right lung of each animal was fixed in 10% neutral buffered formaldehyde and embedded in paraffin. Five-micrometer sections were cut and placed onto positively charged slides. After deparaffinization, sections were incubated with target retrieval solution (Dako, Carpinteria, Calif.) for antigen retrieval. After antibody block, a primary mouse anti-hMPV monoclonal antibody (Virostat, Portland, Me.) was added for 30 min at room temperature, followed by incubation with a biotinylated horse anti-mouse secondary antibody (Vector Laboratories, Burlingame, Calif.). Slides were further incubated with ABC Elite complex to probe biotin (Vector Laboratories) and then developed using a 3,3'-diaminobenzidine (DAB) chromogen kit (Dako) and hematoxylin as a counterstain. Lung sections from hMPV-infected and uninfected samples were used as positive and negative controls, respectively.

Determination of hMPV-neutralizing antibody. hMPV-specific neutralizing antibody titers were determined using a plaque reduction neutralization assay. Briefly, cotton rat sera were collected by retro-orbital bleeding weekly until challenge. The serum samples were heat inactivated at 56° C. for 30 min. Two-fold dilutions of the serum samples were mixed with an equal volume of DMEM containing approximately 100 PFU/well hMPV NL/1/00 in a 96-well plate, and the plate was incubated at room temperature for 1 h with constant rotation. The mixtures were then transferred to confluent Vero E6 cells in a 96-well plate in triplicate. After 1 h of incubation at 37° C., the virus-serum mixtures were removed and the cells were overlaid with 0.75% methylcellulose in DMEM and incubated for another 4 days before virus plaque titration. The plaques were counted and 50% plaque reduction titers were calculated as the hMPV-specific neutralizing antibody titers.

Determination of viral titer in lung and nasal turbinate. The nasal turbinate and the left lung from each cotton rat were removed, weighed, and homogenized in 1 ml of PBS solution using a Precellys 24 tissue homogenizer (Bertin, Md.) following the manufacturer's recommendations. The presence of infectious virus was determined by an immunostaining plaque assay in Vero cells, as described above.

Statistical analysis. Quantitative analysis was performed by either densitometric scanning of autoradiographs or by using a phosphorimager (Typhoon; GE Healthcare, Piscataway, N.J.) and ImageQuant TL software (GE Healthcare, Piscataway, N.J.). Statistical analysis was performed by one-way multiple comparisons using SPSS (version 8.0) statistical analysis software (SPSS Inc., Chicago, Ill.). A P value of <0.05 was considered statistically significant.

Example II

Identification of Amino Acid Residues in hMPV M2-1 Protein Essential for Zinc Binding Activity.

Figure 3A:
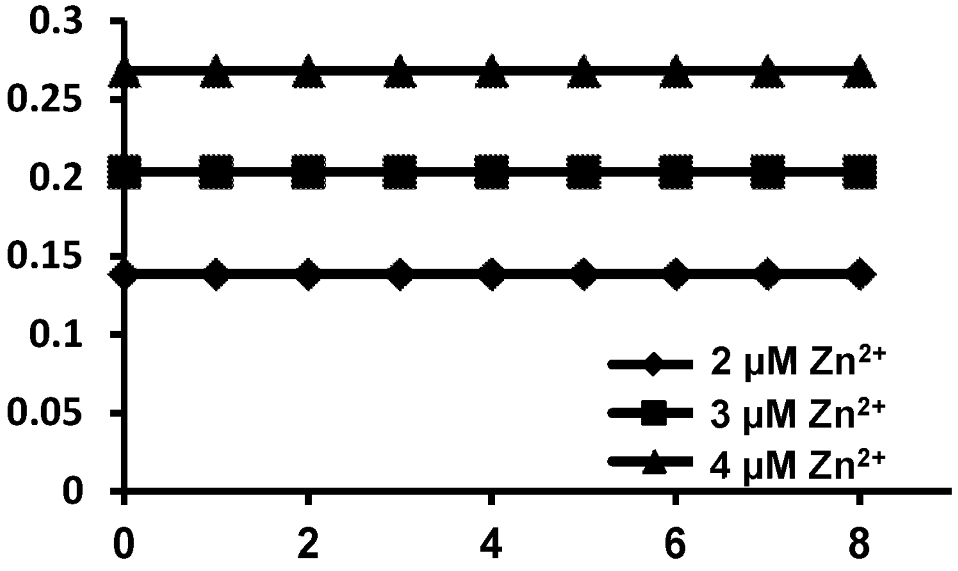
FIG. 3A: Standard curve of zinc ion release. Standard curve generated using 2 μM, 3 μM, and 4 μM ZnSO4.
Figure 3B:
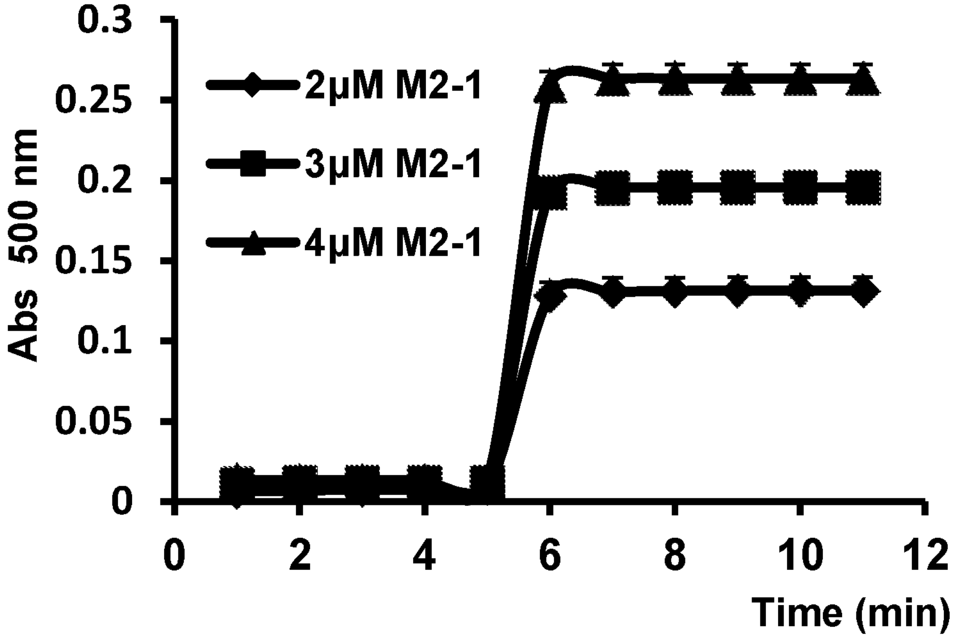
FIG. 3B: Measurement of zinc binding of hMPV M2-1 protein by a colorimetric assay. The amount of Zn2+ bound to hMPV M2-1 protein was quantified by comparing the sample readings to a standard curve.

The amount of zinc bound to the hMPV M2-1 protein was characterized. A time-course colorimetric assay was developed that could directly and quantitatively measure $Zn^{2+}$ binding. Various amounts of highly purified M2-1 protein were incubated with 100 μM 4-(2-Pyridylazo) resorcinol (PAR), the metallochromic indicator, and the release of $Zn^{2+}$ bound to the M2-1 protein was monitored upon addition of 100 μM PMPS. Subsequently, the amount of $Zn^{2+}$ released was determined using standard curves generated by $ZnSO_4$. At concentrations of 2, 3, and 4 μM $Zn^{2+}$, the absorbance at 500 nm was 0.14, 0.20, and 0.27, respectively (FIG. 3A). At concentrations of 2, 3, and 4 μM hMPV M2-1, the absorbance at 500 nm was 0.14, 0.20, and 0.26 upon addition of PMPS (FIG. 3B). Therefore, the molar ratio between hMPV M2-1 and $Zn^{2+}$ released was 1:1; namely, one M2-1 molecule binds to one zinc ion.

Sequence alignment found that M2-1 proteins of all known pneumoviruses possess a putative zinc binding motif (CCCH) (FIG. 1).

Figure 3C:
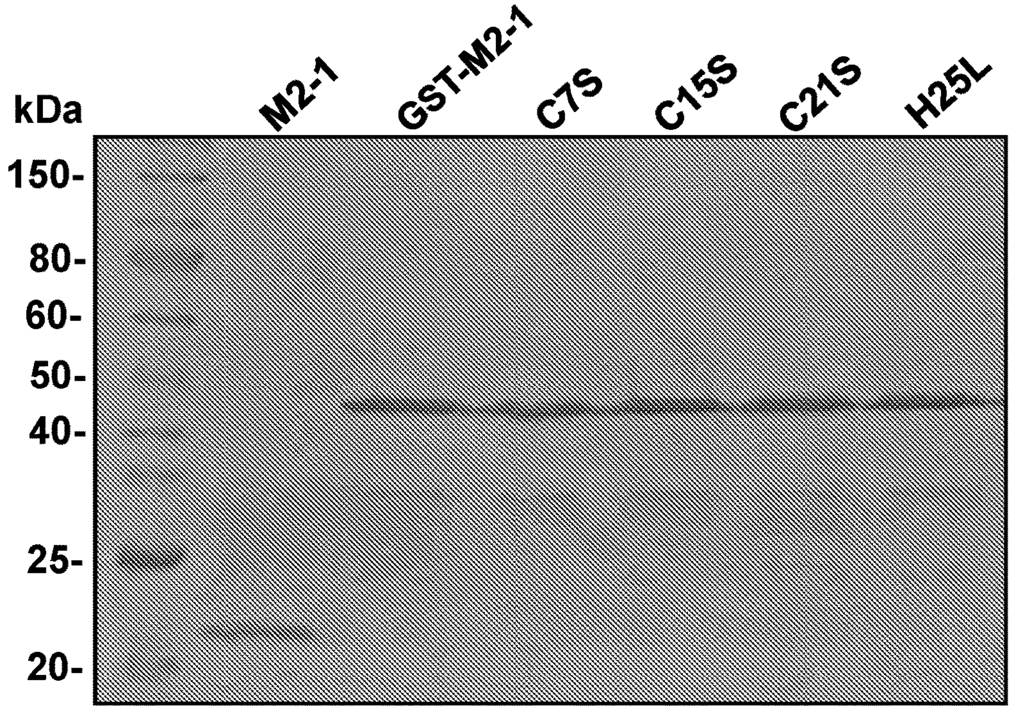
FIG. 3C: Expression and purification of recombinant hMPV M2-1 protein. The GST tagged hMPV M2-1 protein was expressed in *E. coli* Rosetta (DE3) and purified using a column containing Glutathione HiCap Matrix. Where indicated, GST was cleaved from M2-1 by thrombin. Proteins were analyzed by SDS-PAGE.
Figure 3D:
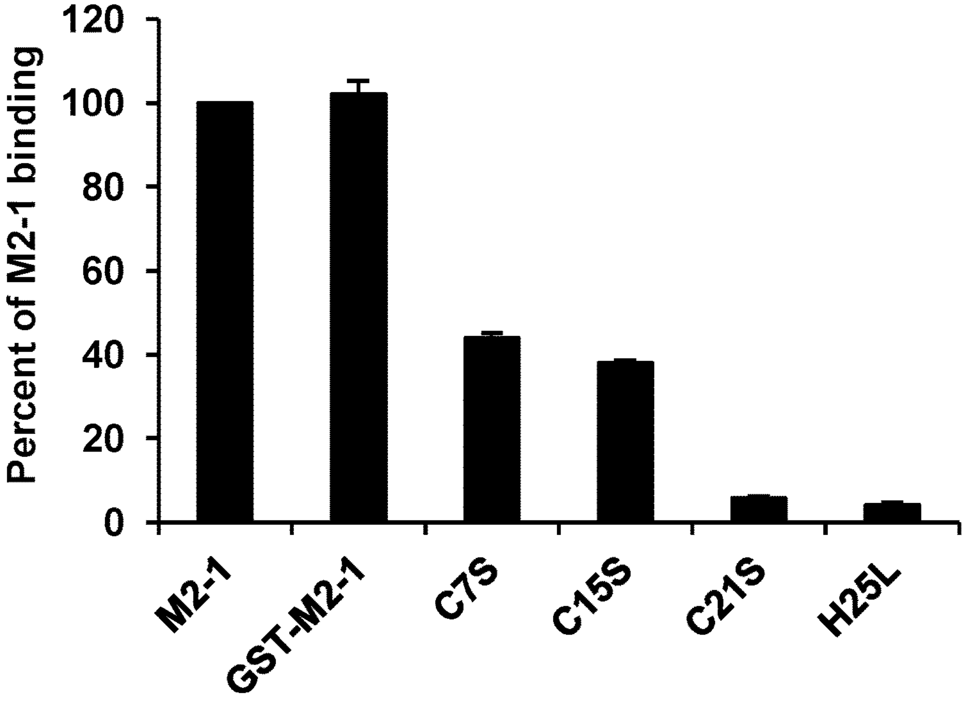
FIG. 3D: Identification of amino acids in M2-1 protein essential for zinc binding activity. The bar graph shows the effect of mutations to zinc binding motif of hMPV M2-1 protein on zinc binding activity. Zinc binding activity was measured by a colorimetric assay. Percent of wild-type M2-1 binding for each M2-1 mutant is shown. The C7S and C15S mutants impaired zinc binding activity by 58% and 62%, respectively, while the C21S and H25L mutants nearly abolished zinc binding. Data were the average of three independent experiments.

It was then determined whether the zinc binding motif is essential for zinc binding activity. Cysteine residues at positions 7, 15 and 21 were changed to serine individually and the histidine at position 25 was changed to leucine. To enhance the solubility of mutant M2-1 proteins, a GST tag was fused to the N terminus of M2-1. All mutant M2-1 proteins were expressed and purified (FIG. 3C). As shown in FIG. 3D, GST-fused rM2-1 (GST-rM2-1) was found to bind the same amount of zinc as rM2-1, demonstrating that the GST tag did not affect the zinc binding activity of the M2-1 protein. Subsequently, the impact of the M2-1 mutations on zinc binding activity was determined. As shown in FIG. 3D, the C7S and C15S mutants impaired zinc binding activity by 58% and 62%, respectively. Notably, the C21S and H25L mutants almost completely abolished zinc binding ability. These results demonstrated that C21 and H25 in the zinc binding motif are essential for zinc binding activity whereas C7 and C15 play minor roles in zinc binding.

Example III

Treatment with EDTA Alters the Secondary Structure of hMPV M2-1.

Having demonstrated that the M2-1 protein coordinates zinc ions, it was then determined whether the secondary structure of M2-1 is altered by EDTA, which can chelate metal ions, including zinc. As shown in FIG. 4A, α-helical signal was detected with two negative maximums at 208 nm and 222 nm using a CD spectroscopy analysis. The secondary structure of hMPV M2-1 at pH 7.4 and 20° C. was dominated by the ordered α-helices (FIG. 4A). The CD spectroscopy showed that the α-helical content gradually decreased when the concentration of EDTA increased from 0 to 20 μM (FIG. 4B). At the maximum metal chelation concentration (20 μM EDTA), the CD spectra were completely altered and did not exhibit a classical α-helix curve (FIG. 4B). These observations indicate that zinc coordination is necessary for the proper folding of hMPV M2-1.

Example IV

Mutations in the Zinc Binding Motif Impair Oligomerization of M2-1 Protein.

The effect of mutations in the zinc binding motif on oligomerization of M2-1 was determined by a chemical cross-linking assay. Briefly, 1.0 μg of rM2-1 protein (without any tag) was cross-linked by an increasing concentration of glutaraldehyde (from 0 to 0.2%) and the resulting products were resolved by SDS-PAGE. As shown in FIG. 5A, protein bands with masses of approximately 40, 60, and 80 kDa were observed when the concentration of glutaraldehyde was increased. Since the native hMPV M2-1 is a 21.3 kDa protein, these bands correlate with the predicted sizes of M2-1 dimers, trimers, and tetramers, respectively (FIG. 5A). No protein bands larger than tetramers were observed even when the concentration of glutaraldehyde was increased above 0.2% with a longer time for cross-linking This is consistent with recent structural studies, which showed that the M2-1 protein is a tetramer. To test whether the GST tag affects the formation of tetramers, the GST-M2-1 was subjected to this cross-linking assay. The predicted product of GST-M2-1 tetramer (196 kDa) was clearly detectable by SDS-PAGE although the predicted dimers and trimers were difficult to visualize (FIG. 5B). This result shows that the GST tag did not affect oligomerization of M2-1.

Subsequently, the effects of mutations in zinc binding motif on oligomerization of M2-1 were examined. The predicted M2-1 tetramer (196 kDa protein) was not observed for C7S, C15S, C21S and H25L (FIG. 5C). This result shows that mutations in the zinc binding motif impair the oligomerization of hMPV M2-1 protein.

Prior to the studies described herein, it was not known whether this zinc binding motif is, indeed, required for zinc coordination. The results described herein show that the third cysteine and the histidine in the zinc binding motif (CCCH) of hMPV M2-1 are crucial for zinc coordination, while the first two cysteine residues each play a minor role in zinc binding. All four M2-1 mutants affected the formation of M2-1 tetramers, suggesting that zinc binding residues are essential for oligomerization of M2-1. The recently-solved structure of hMPV M2-1 showed that the oligomerization domain maps to amino acids 32-58 and that this region folds as an α-helix, which is exposed on the protein surface (FIG. 2 D). However, the CCCH zinc binding motif is physically separated from the oligomerization domain (FIG. 2 D). It is likely that mutations in the zinc binding motif affect local structure, which in turn alters the global structure of the M2-1 protein. In the crystal structure of hMPV M2-1, the cysteine and histidine residues in the zinc binding motif form an extensive hydrogen bond network with side chain-side chain, main chain-side chain, and main chain-main chain interactions (Table 1).

TABLE 1

Interaction of zinc binding motif with other amino acids within M2-1 monomer.

| Amino acids[a] | Hydrogen bond: Main chain-main chain | Hydrogen bond: Main chain-side chain | Hydrogen bond: Side chain-side chain | Ionic interaction |
|---|---|---|---|---|
| C7 | A5(3.34 Å) | Y9(3.46 Å) | C15(3.80 Å) | |
| | Y9(3.23 Å) | E10(3.56 Å) | C21(3.90 Å) | |
| | E10(2.99 Å) | F23(379 Å) | C25(3.63 Å) | |

TABLE 1-continued

Interaction of zinc binding motif with other amino acids within M2-1 monomer.

| Amino acids[a] | Hydrogen bond Main chain-main chain | Main chain-side chain | Side chain-side chain | Ionic interaction |
|---|---|---|---|---|
| | V11(2.99 Å)<br>N24(2.87 Å) | N24(3.58 Å) | | |
| C15 | | E10(3.07 Å)<br>R17(3.80 Å) | C7(3.80 Å)<br>C21(3.86 Å)<br>C25(3.47 Å) | |
| C21 | | F23(3.63 Å) | C7(3.90 Å)<br>C15(3.86 Å)<br>C25(3.59 Å) | |
| H25 | Y27(3.43 Å) | E10(3.80 Å)<br>F23(3.10 Å) | C7(3.63 Å)<br>C15(3.47 Å)<br>C21(3.59 Å) | E10 (3.9 Å) |

[a]Data were collected using hMPV M2-1 structure (PDB ID: 4CS7). C15 is also involved in interprotein interaction between chains in the tetramer. There are four chains (A, B, C, and E) in the tetramer. C15 (chain E) interacts with S75 (chain A); and C15 (chain B) interacts with T76 (chain E).

Example V

Recovery of Recombinant hMPV (rhMPV) Carrying Mutations in the Zinc Binding Motif of M2-1 Protein.

To determine the role of the zinc binding activity in viral replication and pathogenesis, the zinc binding motif of M2-1 in an infectious cDNA clone of hMPV lineage A strain NL/1/00 was mutated. All four recombinant viruses (rhMPV-C7S, C15S, C21S, and H25L) were successfully recovered. The viruses were passed three times in LLC-MK2 cells and stained by a monoclonal antibody against N protein. As shown FIG. 6A, all rhMPV mutants were positive for viral N-protein expression in the immunostaining assay at day 3 post-infection. However, the immunospots formed by these rhMPV mutants in LLC-MK2 cells were smaller than those formed by wt rhMPV, especially those of the C21S and H25L mutants.

The ability of these recombinant viruses to form plaques in LLC-MK2 cells was determined by an agarose overlay plaque assay (FIG. 6B). After 7 days of incubation, the plaque sizes for rhMPV-C7S, C15S, C21S, and H25L were 1.21±0.13, 1.03±0.20, 0.84±0.26, and 0.68±0.11 mm in diameter, respectively, which were all significantly smaller than that of wt rhMPV (1.59±0.31 mm). This demonstrates that rhMPVs carrying mutations in the zinc binding motif had defects in cell-cell spread and/or viral replication in cell culture.

Subsequently, all hMPV mutants were plaque purified. The M2-1 gene of each recombinant virus was amplified by RT-PCR, sequenced, and the presence of the desired mutation was confirmed. Finally, the entire genome of each hMPV mutant was amplified and sequenced. The results showed that no additional mutations were found in the genome except for the introduced mutation in M2-1 gene. These hMPV mutants were passed 10 times in LLC-MK2 cells and sequencing found that all of mutants retained the desired mutation, demonstrating that these zinc binding-defective hMPV mutants are genetically stable in cell culture.

Example VI

Recombinant rhMPV Lacked Zinc Binding Activity Exhibited Delayed Replication, but Grew to a Titer Comparable to that of rhMPV.

The replication kinetics of recombinant hMPV carrying mutations in zinc binding motif were determined in LLC-MK2 cells (FIG. 7). LLC-MK2 cells were infected with each recombinant virus at an MOI of 0.01. At the indicated time points, the amount of virus in the supernatant was determined by immunostaining. Wt rhMPV reached a peak titer of $10^{6.6}$ PFU/ml at day 7 post-inoculation. Recombinant rhMPV-C7S and C15S reached a similar titer at day 8 post-inoculation. Recombinant rhMPV-C21S and H25L showed delayed replication kinetics compared to rhMPV and reached a peak titer of $10^{6.4}$ and $10^{6.1}$ PFU/ml at day 9 post-inoculation, respectively. Recombinant rhMPV-C21S and H25L also had significant delayed cytopathic effects (CPEs) in LLC-MK2 cells. Therefore, although rhMPV-C21S and H25L exhibited a significant delay in viral replication, they grew to a titer comparable to that of wt rhMPV.

Example VII

Recombinant rhMPV Viruses Lacking Zinc Binding Activity were Highly Attenuated in Cotton Rats.

The replication and pathogenesis of rhMPV carrying mutations in the zinc binding motif were determined in cotton rats, the best small animal model available for hMPV. Four-week-old SPF cotton rats were inoculated intranasally with $1.0\times10^{6}$ PFU of wt rhMPV or rhMPV mutants. At day 4 post-inoculation, cotton rats were terminated and viral replication in nasal turbinate and lungs and pulmonary histology were evaluated (Table 2). rhMPV replicated efficiently in the nasal turbinates and lungs of all five cotton rats, with average viral titers of $10^{5.68}$ and $10^{4.25}$ PFU/g tissue, respectively. Recombinant rhMPV-C7S and C15S, which retained 60% of zinc binding activity, replicated as efficiently as rhMPV in cotton rats, producing similar titers in both the nasal turbinates and the lungs of all five cotton rats (P>0.05). Recombinant rhMPV-C21S and H25L, which abolished zinc binding activity, were highly attenuated in replication in cotton rats. No infectious virus was detected in either nasal turbinate or lungs in rhMPV-C21S infected cotton rats. Only one out of five cotton rats had a low level of infectious virus ($10^{2.3}$ PFU/ml) in nasal turbinate and no infectious virus was found in lungs.

Pulmonary histology showed that rhMPV caused moderate histological lesions, including interstitial pneumonia, peribronchial lymphoplasmacytic infiltrates, mononuclear cell infiltrate, and edematous thickening of the bronchial submucosa (FIG. 8). Recombinant rhMPV-C7S and C15S caused similar histologic lesions compared to rhMPV. In contrast, rhMPV-C21S and H25L caused no or only mild pulmonary histological changes (FIG. 8). Immunohistobiochemistry analysis found that lungs of cotton rats infected by rhMPV contained a large amount of viral antigen in epithelial cells. The viral antigen expression of rhMPV-C7S and C15S in lung epithelial cells was similar to that of wt rhMPV (FIG. 9). In contrast, no viral antigen was found in the lungs of cotton rats infected by rhMPV-C21S and H25L (FIG. 9).

Taken together, these results showed that rhMPV-C7S and C15S replicated efficiently in cotton rats and caused similar histologic lesions as rhMPV, whereas rhMPV-C21S and H25L were highly attenuated in replication in both the upper and lower respiratory tracts of cotton rats.

Along with the data discussed in Example V, these results show that the zinc binding activity of hMPV M2-1 is dispensable for viral replication in vitro, but essential for viral replication and pathogenesis in vivo. Zinc binding-deficient rhMPVs were highly attenuated in replication in vitro cell culture and in vivo cotton rats and did not cause lung histologic lesion. In contrast, rhMPVs retaining 60% of zinc binding activity were capable of replicating as efficiently as wild-type hMPV in vitro and in vivo, and caused significant lung damage.

TABLE 2

Replication of rhMPV carrying mutations in zinc binding motif in cotton rats.

| Mutant [A] | Number of cotton rats per group | Viral replication in nasal turbinate [B] % of infected animals | Viral replication in nasal turbinate [B] Mean titer log (PFU/g) | Viral replication in lung % of infected animals | Viral replication in lung Mean titer log (PFU/g) | Lung histology [C] | Lung IHC [D] |
|---|---|---|---|---|---|---|---|
| rhMPV | 5 | 100 | $5.68 \pm 0.36^a$ | 100 | $4.25 \pm 0.43^a$ | $1.8^a$ | $3.0^a$ |
| rhMPV-C7S | 5 | 100 | $5.31 \pm 0.60^a$ | 100 | $4.14 \pm 0.34^a$ | $1.5^a$ | $2.5^a$ |
| rhMPV-C15S | 5 | 100 | $5.56 \pm 0.39^a$ | 100 | $4.08 \pm 0.47^a$ | $1.6^a$ | $2.5^a$ |
| rhMPV-C21S | 5 | 0 | ND | 0 | ND | $0.5^b$ | $0^b$ |
| rhMPV-H25F | 5 | 20 | 2.3 | 0 | ND | $0.8^b$ | $0.5^b$ |

[A] Cotton rats were inoculated intranasally with DMEM or $2 \times 10^5$ pfu wild-type rhMPV or rhMPV mutants. At day 4 post immunization, animals were euthanized for pathology study.
[B] For rhMPV-H25L, 1 out of 5 cotton rats had detectable virus with a titer of 2.3 log PFU/g. "ND" indicates that infectious virus was not detectable. Value within a column followed by the different lowercase letters (a and b) are significantly different ($P < 0.05$).
[C] The severity of lung histology was scored for each lung tissue. Average score for each group was shown. 0 = no change; 1 = mild change; 2 = moderate change; and 3 = severe change.
[D] The amount of hMPV antigen expression in lung was scored. Average score for each group was shown. 0 = no antigen; 1 = small amount; 2 = moderate amount; and 3 = large amount.

Example VIII

Recombinant rhMPVs Lacking Zinc Binding Activity were Highly Immunogenic and Protected Cotton Rats from hMPV Infection.

The immunogenicity of the two attenuated mutants (rhMPV-C21S and H25L) was determined by vaccination of cotton rats, followed by challenge with rhMPV. After vaccination, serum antibody levels were determined weekly by a plaque reduction neutralization assay. As shown in FIG. 10, rhMPV-C21S and H25L triggered high levels of neutralizing antibody that were comparable to those generated after wt rhMPV immunization (P>0.05). Antibody was detectable at week 1 post-immunization, and the levels gradually increased during weeks 2 to 4. No hMPV-specific antibody was detected in the unvaccinated control.

At week 4 post-immunization, all vaccinated cotton rats were challenged with wt rhMPV and cotton rats were terminated at day 4 post-inoculation. No infectious virus was detectable in either nasal turbinates or lungs from the animals vaccinated with either rhMPV-C21S or H25L, followed by rhMPV challenge (Table 3). Pulmonary histology showed that the unvaccinated challenged control had moderate pathological changes characterized by interstitial pneumonia, mononuclear cell infiltrate, and edematous thickening of the bronchial submucosa. In contrast, no or only mild histological changes were found in the lungs of cotton rats vaccinated with rhMPV-C21S and rhMPV-H25L (Table 3). No enhanced lung damage was found for the mutants. IHC showed that large numbers of viral antigens were found at the luminal surface of the bronchial epithelial cells in lung tissues from unvaccinated challenged controls (FIG. 11). In contrast, no antigens were found on the luminal surface of bronchial epithelial cells in the rhMPV-C21S and rhMPV-H25L groups (FIG. 11). Instead, antigen was found within bronchial tissue, which was related to viral clearance.

TABLE 3

Immunogenicity of rhMPV lacking zinc binding activity in cotton rats.

| Mutant [A] | Number of cotton rats per group | Nasal turbinate [B] % of infected animals | Nasal turbinate [B] Mean titer log (PFU/g) | Lung % of infected animals | Lung Mean titer log (PFU/g) | Lung histology [C] |
|---|---|---|---|---|---|---|
| DMEM | 5 | 100 | 4.82 ± 0.19 | 100 | 4.34 ± 0.20 | 2.0[a] |
| rhMPV | 5 | 0 | ND | 0 | ND | 0.8[b] |
| rhMPV-C21S | 5 | 0 | ND | 0 | ND | 0.6[b] |
| rhMPV-H25L | 5 | 0 | ND | 0 | ND | 0.5[b] |

[A] Animals were immunized intranasally with DMEM or $2 \times 10^5$ pfu wild-type rhMPV or rhMPV mutants. At day 28 post immunization, animals were challenged with $1 \times 10^6$ pfu wild-type rhMPV.
[B] ND indicates infectious virus was not detectable.
[C] The severity of lung histology was scored for each lung tissues. Average score for each group was shown. 0 = no change; 1 = mild change; 2 = moderate change; and 3 = severe change. Value within a column followed by the different lowercase letters (a and b) are significantly different ($P < 0.05$).

Collectively, these results demonstrate that rhMPVs lacking zinc binding activity are not only sufficiently attenuated, but also capable of triggering high levels of antibody and providing protection against viral challenge by hMPV.

These zinc binding-deficient rhMPVs are ideal live attenuated vaccines. These two rhMPV mutants grow to high titers in cell culture, making it economically feasible for vaccine production. No revertants or additional mutations were detected after ten passages of these mutants in cell culture, showing that they are genetically stable. Importantly, these two rhMPV mutants were sufficiently attenuated, yet retained high immunogenicity.

Previously, it was shown that rhMPV lacking the entire M2-1 gene (rhMPVΔM2-1) was overly attenuated so that it failed to trigger either an hMPV-specific antibody response or protective immunity in animals (Buchholz U J et al., 2005. *Deletion of M2 gene open reading frames* 1 *and* 2 *of human metapneumovirus: effects on RNA synthesis, attenuation, and immunogenicity.* J Virol 79:6588-97). In contrast to rhMPVΔM2-1, rhMPVs lacking zinc binding activity described herein were defective in replication in the upper and lower respiratory tracts of cotton rats, but were capable of inducing high levels of neutralizing antibody and providing protection against subsequent challenge by rhMPV.

Example IX

Materials and Methods—Human Respiratory Syncytial Virus

Cell lines. HEp-2 and Hela cells were maintained in Opti-MEM medium (Life Technologies, Bethesda, Md.) supplemented with 10% fetal bovine serum (FBS).

Plasmids and site-directed mutagenesis. Plasmids encoding the hRSV minigenome (MP169) expressing the green fluorescent protein (GFP) and the full-length genomic cDNA of hRSV strain A2 (RW30) are modified versions of plasmids provided by Peter Collins (National Institutes of Health). Peter Collins also provided the support plasmids expressing RSV N protein (pN), P protein (pP), L protein (pL), and M2-1 protein (pM2-1). MVA-T7, a vaccinia virus derivative expressing the T7 polymerase was provided by Bernard Moss. The M2-1 mutants of RSV were generated by site-directed mutagenesis using QuikChange (Stratagene, La Jolla, Calif.). All constructs were sequenced to confirm the presence of the introduced mutations.

Expression and purification of recombinant RSV M2-1 protein from *E.coli*. The RSV M2-1 gene was PCR amplified from the RW30 cDNA clone of strain A2 and was inserted into the *E. coli* expression plasmid pGEX-4T-1 at the BamHI and NotI sites. To facilitate protein purification, the GST sequence was fused to the N-terminus of the M2-1 gene. The resulting plasmids were transformed into *E. coli* Rosetta (DE3) and grown at 37° C. until the absorbance at 600 nm reached 0.6-0.8. Cells were chilled on ice for 10 min and protein expression was induced by the addition of 20 μM Isopropyl β-D-1-thiogalactopyranoside (IPTG) and 75 μM ZnSO4. The cells were grown for an additional 20 h at 25° C. and harvested by centrifugation at 5,000 g for 10 mM. Bacterial pellets were resuspended in lysis buffer [40 mM Tris-HCl (pH 7.4), 1.0 M NaCl, 0.5 mM DTT, and 20 μM ZnSO4] supplemented with 1 mg/ml of lysozyme and protease inhibitor cocktail (Roche, Mannheim, Germany). After 30 min incubation on ice, the cells were lysed using sonication, followed by centrifugation at 15,000 g at 4° C. for 40 min. The supernatant was collected and loaded into a column containing 5 ml of Glutathione HiCap Matrix (Qiagen).

The G resin was washed with 150 ml of resuspension buffer, followed by washing with 100 ml of cleavage buffer (50 mM Tris-HCl (pH 7.6), 2.5 mM CaCl2, 150 mM NaCl, and 0.2 mM DTT). To isolate GST-free M2-1, 20 ml of the cleavage buffer containing 2 units/ml of thrombin (Sigma, St. Louis, Mo.) was loaded into the column and was incubated at room temperature for 8 h. Cleavage was halted by adding APMSF (Sigma). Similarly, the GST fusion RSV M2-1 mutants C7S, C15S, C21S and H25L were generated. The purified RSV M2-1 proteins were dialyzed against PBS buffer containing 300 mM NaCl and 10 μM ZnSO4. Protein concentration was determined by the Bradford assay (Sigma).

Colorimetric determination of the zinc content. Purified RSV M2-1 was dialyzed against 50 mM PBS (pH 7.0) containing 0.3 M NaCl at 4° C. overnight. RSV M2-1 proteins at concentrations of 2 μM, 3 μM, and 4 μM in a 1 ml of solution containing 100 μM 4-(2-Pyridylazo) resorcinol (PAR) were incubated at 25° C. for 20 min and the absorbance at 500 nm was monitored for 5 min. Upon addition of 100 μM p-chloromercuriphenylsulfonic acid (PMPS), the release of strongly bound $Zn^{2+}$ was monitored. The amount of $Zn^{2+}$ bound to RSV M2-1 was quantified by comparing the sample readings to a standard curve generated using 2 μM, 3 μM, and 4 μM $ZnSO_4$ (Sigma). Buffer containing 50 mM PBS (pH7.0), 0.3 M NaCl, and 100 μM PAR was used as the blank control. The zinc ion content of GST-M2-1 and mutants were measured at 2 μM and compared with rM2-1 at the same zinc concentration.

Recovery of recombinant RSV-GFP (rgRSV) from the full-length cDNA clones. The full-length cDNA clones carrying wild-type M2-1 and M2-1 with mutations in its zinc binding motif were rescued as replicating rgRSV using the reverse genetics system. HEp-2 cells were infected with MVA-T7 at an MOI of 0.1. At 1 h post-infection, cells were transfected with 5.0 μg of plasmid RW30 carrying the full-length RSV genome, 2.0 μg of pN, 2.0 μg of pP, 1.0 μg of pL, and 1.0 μg of pM2-1 using Lipofectamine 2000 (Life Technologies). At day 4 posttransfection, the cells were harvested using scrapers and were cocultured with fresh HEp-2 cells at 50-60% confluence. When extensive cytopathic effects (CPE) were observed, the cells were subjected to three freeze-thaw cycles, followed by centrifugation at 3,000×g for 10 min. The supernatant was subsequently used to infect fresh HEp-2 cells. The successful recovery of the rgRSVs was confirmed by plaque assay and reverse transcription (RT)-PCR.

Viral replication kinetics in HEp-2 cells. Confluent HEp-2 cells in 35-mm dishes were infected with wild-type (wt) or mutant rgRSV at an MOI of 0.01. After 1 h of adsorption, the inoculum was removed and the cells were washed three times with PBS. Fresh DMEM (supplemented with 2% FBS) was added and the infected cells were incubated at 37° C. At different time points postinfection, the expression of GFP by each rgRSV was photographed.

Example X

Expression of RSV M2-1 and Mutant M2-1 Proteins.

To determine the zinc binding activity of RSV M2-1, the recombinant RSV M2-1 (rM2-1) protein was expressed in *E. coli*. To facilitate the purification of RSV M2-1, a GST tag was fused to its N terminus. As shown in FIG. 12, rM2-1 protein can be expressed and purified. Sequence alignment indicated that all known pneumovirus M2-1 proteins, like the RSV M2-1 protein, possess a putative zinc binding motif (C7-C15-C21-H25; FIG. 1) near its N-terminus. To analyze the role of these amino acid residues in zinc binding, the cysteine residues at positions 7, 15 and 21 were individually changed to serine and the histidine at position 25 was changed to leucine. Four M2-1 mutants—C7S, C15S, C21S, and H25—were generated and expressed in *E.coli* as GST fusion proteins. As shown in FIG. 12, all four mutant M2-1 proteins were expressed, recovered, and purified.

Example XI

Mutations in the Zinc Binding Motif of RSV M2-1 Diminish the Zinc Binding Activity. As described above, C7S and C15S mutants of hMPV M2-1 impaired zinc binding activity by 58% and 62%, respectively, and C21S and H25L mutants of hMPV M2-1 nearly abolished zinc binding ability. To determine the impact of mutations on zinc binding activity of RSV M2-1, equal amounts of wild-type RSV rM2-1 and mutant M2-1 proteins were subjected to a colorimetric zinc binding assay. RSV M2-1 C15S mutant retained 80% of zinc binding activity whereas C15S, C21S, and H25L mutants retained approximately 60% of zinc binding activity compared to wild type rM2-1 protein (FIG. 13). Thus, these results showed that mutations to zinc binding motif of the RSV M2-1 protein diminished the zinc binding activity of the M2-1 protein.

Example XII

Recovery of Recombinant RSVs Carrying Mutations in Zinc Binding Motif.

Unlike the hMPV M2-1 protein, the hRSV M2-1 protein is essential for virus replication. First, it was previously shown that deletion of the entire M2-1 or partial deletions in M2-1 were lethal to hRSV (Collins P L, Camargo E, and Hill M G, 1999. *Support plasmids and support proteins required for recovery of recombinant respiratory syncytial virus.* Virology 259:251-5; Collins P L et al., 1995. *Production of infectious human respiratory syncytial virus from cloned cDNA confirms an essential role for the transcription elongation factor from the 5' proximal open reading frame of the M2 mRNA in gene expression and provides a capability for vaccine development.* PNAS USA 92:11563-67; Tang R S et al., 2001. *Requirement of cysteines and length of the human respiratory syncytial virus M2-1 protein function and virus availability.* J. Virol. 75:11328-35). This result is consistent with the processivity function of M2-1. Second, it was also shown that single amino acid substitutions (C to G) in the first three cysteine residues (namely C7G, C15G, and C21G) were lethal to RSV, preventing recovery of the recombinant virus. Until the present studies, the impact of mutations in H25 on the hRSV life cycle had not been studied.

As described and shown herein, a different mutagenesis strategy was followed. Namely, the first three cysteine residues of M2-1, at positions 7, 15 and 21, were changed to serine individually, and the histidine at position 25 was changed to leucine. Each of these mutations were inserted individually into an infectious cDNA clone of RSV with GFP inserted as the first gene, between the leader and N gene of RW30. All four recombinant viruses (rgRSV-C7S, C15S, C21S, and H25L) were recovered. As shown in FIG. 3, rgRSV-C21S and H25L had a delayed GFP expression and had delayed cytopathic effects (CPE) in cell culture, demonstrating that these recombinant viruses are attenuated in vitro.

While the invention has been described with reference to various embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiments disclosed herein contemplated for carrying out this invention, but that the invention will include all embodiments falling within the scope of the claims.

What is claimed is:

1. An attenuated recombinant *pneumovirus* comprising a mutated zinc binding domain in an M2-1 protein of the *pneumovirus*, wherein at least one amino acid of the zinc binding domain is mutated relative to wildtype *pneumovirus*, and wherein the at least one amino acid mutation comprises at least one of C21S and H25L.

2. The attenuated recombinant *pneumovirus* of claim 1, wherein the at least one amino acid mutation in the zinc binding domain is non-lethal and abolishes zinc binding activity of the M2-1 protein.

3. The attenuated recombinant *pneumovirus* of claim 1, wherein the at least one amino acid mutation further comprises at least one of C7S and C15S.

4. The attenuated recombinant *pneumovirus* of claim 1, wherein the mutated zinc binding domain comprises at least one amino acid mutation at an amino acid selected from the group consisting of: C21; and H25, and at least one amino acid mutation at an amino acid selected from the group consisting of: C7 and C15.

5. The attenuated recombinant *pneumovirus* of claim 1, wherein the *pneumovirus* is selected from the group consisting of: human *metapneumovirus*; avian *metapneumovirus*; human respiratory syncytial virus; bovine respiratory syncytial virus; and pneumonia virus of mice.

6. The attenuated recombinant *pneumovirus* of claim 1, wherein the *pneumovirus* is a *metapneumovirus* or a respiratory syncytial virus.

7. A vaccine composition comprising the attenuated recombinant *pneumovirus*of claim 1.

8. The vaccine composition of claim 7, further comprising at least one of a pharmaceutically acceptable carrier, a pharmaceutically acceptable vehicle, a pharmaceutically acceptable excipient, and a pharmaceutically acceptable adjuvant.

9. A method for inducing a protective immune response in a subject, comprising administering to the subject an immunologically effective dose of the vaccine composition of claim 7.

10. The method of claim 9, wherein the vaccine composition is administered via an administration route selected from the group consisting of: intranasal administration; subcutaneous administration; intramuscular administration; intradermal administration; and oral administration.

11. The method of claim 9, further comprising administering at least one subsequent immunologically effective dose of the vaccine composition.

12. The method of claim 11, wherein the at least one subsequent dose is administered at an interval selected from the group consisting of: approximately one week after the first dose; approximately two weeks after the first dose; approximately three weeks after the first dose; approximately four weeks after the first dose; approximately five weeks after the first dose; approximately six weeks after the first dose; approximately seven weeks after the first dose; and approximately eight weeks after the first dose.

13. The method of claim 9, wherein the subject is an individual selected from the group consisting of: humans; fowl; cattle; and rodents.

14. The method of claim 9, wherein the protective immune response protects the subject from viral challenge by a virus selected from the group consisting of: human *metapneumovirus*subtype A; human *metapneumovirus* subtype B; avian *metapneumovirus* subtype A; avian *metapneumovirus* subtype B; avian *metapneumovirus* subtype C; avian *metapneumovirus* subtype D; human respiratory syncytial virus type A; human respiratory syncytial virus type B; bovine respiratory syncytial virus; and pneumonia virus of mice.

15. A method for preparing the vaccine composition of claim 7, comprising mixing the attenuated recombinant *pneumovirus* of claim 1 with at least one of a pharmaceutically acceptable carrier, a pharmaceutically acceptable vehicle, a pharmaceutically acceptable excipient, and a pharmaceutically acceptable adjuvant.

16. The method of claim 15, wherein the vaccine composition is formulated for administration via an administration route selected from the group consisting of: intranasal administration; subcutaneous administration; intramuscular administration; intradermal administration; and oral administration.

17. A kit comprising the vaccine composition of claim 7, and at least one container.

* * * * *

SEQUENCE LISTING

```
<160> NUMBER OF SEQ ID NOS: 9

<210> SEQ ID NO 1
<211> LENGTH: 187
<212> TYPE: PRT
<213> ORGANISM: Human metapneumovirus

<400> SEQUENCE: 1

Met Ser Arg Lys Ala Pro Cys Lys Tyr Glu Val Arg Gly Lys Cys Asn
1               5                   10                  15

Arg Gly Ser Glu Cys Lys Phe Asn His Asn Tyr Trp Ser Trp Pro Asp
            20                  25                  30

Arg Tyr Leu Leu Ile Arg Ser Asn Tyr Leu Leu Asn Gln Leu Leu Arg
        35                  40                  45

Asn Thr Asp Arg Ala Asp Gly Leu Ser Ile Ile Ser Gly Ala Gly Arg
    50                  55                  60

Glu Asp Arg Thr Gln Asp Phe Val Leu Gly Ser Thr Asn Val Val Gln
65                  70                  75                  80

Gly Tyr Ile Asp Asp Asn Gln Ser Ile Thr Lys Ala Ala Ala Cys Tyr
                85                  90                  95

Ser Leu His Asn Ile Ile Lys Gln Leu Gln Glu Val Glu Val Arg Gln
            100                 105                 110

Ala Arg Asp Ser Lys Leu Ser Asp Ser Lys His Val Ala Leu His Asn
        115                 120                 125

Leu Ile Leu Ser Tyr Met Glu Met Ser Lys Thr Pro Ala Ser Leu Ile
    130                 135                 140

Asn Asn Leu Lys Arg Leu Pro Arg Glu Lys Leu Lys Lys Leu Ala Lys
145                 150                 155                 160

Leu Ile Ile Asp Leu Ser Ala Gly Ala Asp Asn Asp Ser Ser Tyr Ala
                165                 170                 175

Leu Gln Asp Ser Glu Ser Thr Asn Gln Val Gln
            180                 185


<210> SEQ ID NO 2
<211> LENGTH: 187
<212> TYPE: PRT
<213> ORGANISM: Human metapneumovirus

<400> SEQUENCE: 2

Met Ser Arg Lys Ala Pro Cys Lys Tyr Glu Val Arg Gly Lys Cys Asn
1               5                   10                  15

Arg Gly Ser Glu Cys Lys Phe Asn His Asn Tyr Trp Ser Trp Pro Asp
            20                  25                  30

Arg Tyr Leu Leu Leu Arg Ser Asn Tyr Leu Leu Asn Gln Leu Leu Arg
        35                  40                  45

Asn Thr Asp Lys Ala Asp Gly Leu Ser Ile Ile Ser Gly Ala Gly Arg
    50                  55                  60

Glu Asp Arg Thr Gln Asp Phe Val Leu Gly Ser Thr Asn Val Val Gln
65                  70                  75                  80

Gly Tyr Ile Asp Asn Asn Gln Gly Ile Thr Lys Ala Ala Ala Cys Tyr
                85                  90                  95
```

```
Ser Leu His Asn Ile Ile Lys Gln Leu Gln Glu Ile Glu Val Arg Gln
            100                 105                 110

Ala Arg Asp Asn Lys Leu Ser Asp Ser Lys His Val Ala Leu His Asn
        115                 120                 125

Leu Ile Leu Ser Tyr Met Glu Met Ser Lys Thr Pro Ala Ser Leu Ile
    130                 135                 140

Asn Asn Leu Lys Lys Leu Pro Arg Glu Lys Leu Lys Lys Leu Ala Lys
145                 150                 155                 160

Leu Ile Ile Asp Leu Ser Ala Gly Thr Asp Asn Asp Ser Ser Tyr Ala
                165                 170                 175

Leu Gln Asp Ser Glu Ser Thr Asn Gln Val Gln
            180                 185


<210> SEQ ID NO 3
<211> LENGTH: 186
<212> TYPE: PRT
<213> ORGANISM: Avian metapneumovirus

<400> SEQUENCE: 3

Met Ser Arg Arg Asn Pro Cys Arg Tyr Glu Ile Arg Gly Lys Cys Asn
1               5                   10                  15

Arg Gly Ser Ser Cys Thr Phe Asn His Asn Tyr Trp Ser Trp Pro Asp
            20                  25                  30

His Val Leu Leu Val Arg Ala Asn Tyr Met Leu Asn Gln Leu Leu Arg
        35                  40                  45

Asn Thr Asp Arg Thr Asp Gly Leu Ser Leu Ile Ser Gly Ala Gly Arg
    50                  55                  60

Glu Asp Arg Thr Gln Asp Phe Val Leu Gly Ser Ala Asn Val Val Gln
65                  70                  75                  80

Asn Tyr Ile Glu Gly Asn Thr Thr Ile Thr Lys Ser Ala Ala Cys Tyr
                85                  90                  95

Ser Leu Tyr Asn Ile Ile Lys Gln Leu Gln Glu Asn Asp Val Lys Thr
            100                 105                 110

Ser Arg Asp Ser Met Leu Glu Asp Pro Lys His Val Ala Leu His Asn
        115                 120                 125

Leu Ile Leu Ser Tyr Val Asp Met Ser Lys Asn Pro Ala Ser Leu Ile
    130                 135                 140

Asn Ser Leu Lys Arg Leu Pro Arg Glu Lys Leu Lys Lys Leu Ala Lys
145                 150                 155                 160

Ile Ile Leu Gln Leu Ser Ala Gly Pro Glu Ser Asp Asn Ala Ser Gly
                165                 170                 175

Asn Thr Leu Gln Lys Gly Asp Ser Asn Asn
            180                 185


<210> SEQ ID NO 4
<211> LENGTH: 186
<212> TYPE: PRT
<213> ORGANISM: Avian metapneumovirus

<400> SEQUENCE: 4

Met Ser Arg Arg Asn Pro Cys Arg Tyr Glu Thr Arg Gly Lys Cys Asn
1               5                   10                  15

Arg Gly Ser Ser Cys Thr Phe Asn His Asn Tyr Trp Ser Trp Pro Asp
            20                  25                  30

His Val Leu Leu Val Arg Ala Asn Tyr Met Leu Asn Gln Leu Val Arg
        35                  40                  45
```

-continued

Asn Thr Asp Arg Thr Asp Gly Leu Ser Leu Ile Ser Gly Ala Gly Arg
50 55 60

Glu Asp Arg Thr Gln Asp Phe Val Leu Gly Ser Ala Asn Val Val Gln
65 70 75 80

Asn Tyr Ile Glu Gly Asn Ala Thr Ile Thr Lys Ser Ala Ala Cys Tyr
85 90 95

Ser Leu Tyr Asn Ile Ile Lys Gln Leu Gln Glu Asn Asp Val Lys Ser
100 105 110

Ala Arg Asp Leu Met Val Asp Asp Pro Lys His Val Ala Leu His Asn
115 120 125

Leu Val Leu Ser Tyr Ile Asp Met Ser Lys Asn Pro Ala Asn Leu Ile
130 135 140

Asn Ser Leu Lys Arg Leu Pro Lys Glu Lys Leu Lys Lys Leu Ala Lys
145 150 155 160

Ile Ile Ile Gln Leu Ser Ala Gly Ser Glu Gly Glu Asn Ala Asn Ser
165 170 175

Asn Thr Leu Gln Lys Gly Asp Ser Ser Asn
180 185

<210> SEQ ID NO 5
<211> LENGTH: 184
<212> TYPE: PRT
<213> ORGANISM: Avian metapneumovirus

<400> SEQUENCE: 5

Met Ser Arg Lys Ala Pro Cys Lys Tyr Glu Val Arg Gly Lys Cys Asn
1 5 10 15

Arg Gly Ser Glu Cys Lys Phe Asn His Asn Tyr Trp Asn Trp Pro Asp
20 25 30

Arg Tyr Leu Leu Leu Arg Ser Asn Tyr Leu Leu Asn Gln Leu Leu Arg
35 40 45

Asn Thr Asp Arg Ser Asp Gly Leu Ser Leu Ile Ser Gly Ala Gly Arg
50 55 60

Asp Asp Arg Thr Gln Asp Phe Val Leu Gly Ser Thr Asn Val Val Gln
65 70 75 80

Asn Tyr Ile Asp Asn Asn Glu Asn Ile Thr Lys Ala Ser Ala Cys Tyr
85 90 95

Ser Leu Tyr Asn Ile Ile Lys Gln Leu Gln Glu Thr Asp Val Arg Gln
100 105 110

Ala Arg Asp Asn Lys Val Asp Asp Ser Lys His Val Ala Leu His Asn
115 120 125

Leu Val Leu Ser Tyr Met Glu Met Ser Lys Thr Pro Ala Ser Leu Ile
130 135 140

Asn Asn Leu Lys Lys Leu Pro Lys Glu Lys Leu Lys Lys Leu Ala Lys
145 150 155 160

Leu Ile Ile Glu Leu Ser Ala Gly Val Glu Asn Asp Ser Thr Ala Ala
165 170 175

Met Gln Asp Ser Ala Asn Ser Asp
180

<210> SEQ ID NO 6
<211> LENGTH: 194
<212> TYPE: PRT
<213> ORGANISM: Human respiratory syncytial virus

<400> SEQUENCE: 6

-continued

```
Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Ser Thr Val Ser Asp Thr Asn Asp His Ala Lys Asn Asn Asp
            180                 185                 190

Thr Thr


<210> SEQ ID NO 7
<211> LENGTH: 195
<212> TYPE: PRT
<213> ORGANISM: Human respiratory syncytial virus

<400> SEQUENCE: 7

Met Ser Arg Arg Asn Pro Cys Lys Phe Glu Ile Arg Gly His Cys Leu
1               5                   10                  15

Asn Gly Arg Arg Cys His Tyr Ser His Asn Tyr Phe Glu Trp Pro Pro
            20                  25                  30

His Ala Leu Leu Val Arg Gln Asn Phe Met Leu Asn Lys Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Ile Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Ile Glu Ile Asn Ser Asp Asp Ile Lys
            100                 105                 110

Lys Leu Arg Asp Asn Glu Glu Pro Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Ile Ile Ser Asn Pro
                165                 170                 175
```

-continued

```
Lys Glu Ser Thr Val Asn Asp Gln Asn Asp Gln Thr Lys Asn Asn Asp
            180                 185                 190

Ile Thr Gly
        195


<210> SEQ ID NO 8
<211> LENGTH: 186
<212> TYPE: PRT
<213> ORGANISM: Bovine respiratory syncytial virus

<400> SEQUENCE: 8

Met Ser Arg Arg Asn Pro Cys Lys Tyr Glu Ile Arg Gly His Cys Leu
1               5                   10                  15

Asn Gly Lys Lys Cys His Phe Ser His Asn Tyr Phe Glu Trp Pro Pro
            20                  25                  30

His Ala Leu Leu Val Arg Gln Asn Phe Met Leu Asn Lys Ile Leu Lys
        35                  40                  45

Ser Met Asp Arg Asn Asn Asp Thr Leu Ser Glu Ile Ser Gly Ala Ala
    50                  55                  60

Glu Leu Asp Arg Thr Glu Glu Tyr Ala Leu Gly Val Ile Gly Val Leu
65                  70                  75                  80

Glu Ser Tyr Leu Ser Ser Ile Asn Asn Ile Thr Lys Gln Ser Ala Cys
                85                  90                  95

Val Ala Met Ser Lys Leu Leu Ala Glu Ile Asn Asn Asp Asp Ile Lys
            100                 105                 110

Arg Leu Arg Asn Lys Glu Val Pro Thr Ser Pro Lys Ile Arg Ile Tyr
        115                 120                 125

Asn Thr Val Ile Ser Tyr Ile Asp Ser Asn Lys Arg Asn Thr Lys Gln
    130                 135                 140

Thr Ile His Leu Leu Lys Arg Leu Pro Ala Asp Val Leu Lys Lys Thr
145                 150                 155                 160

Ile Lys Asn Thr Ile Asp Ile His Asn Glu Ile Asn Gly Asn Asn Gln
                165                 170                 175

Gly Asp Ile Asn Val Asp Glu Gln Asn Glu
            180                 185


<210> SEQ ID NO 9
<211> LENGTH: 176
<212> TYPE: PRT
<213> ORGANISM: Pneumonia virus
<220> FEATURE:
<223> OTHER INFORMATION: Pneumonia virus of mice

<400> SEQUENCE: 9

Met Ser Val Arg Pro Cys Lys Phe Glu Val Gln Gly Phe Cys Ser Arg
1               5                   10                  15

Gly Arg Asn Cys Lys Tyr Ser His Lys Tyr Trp Glu Trp Pro Leu Lys
            20                  25                  30

Thr Leu Met Leu Arg Gln Asn Tyr Met Leu Asn Arg Ile Tyr Arg Phe
        35                  40                  45

Leu Asp Thr Asn Thr Asp Ala Met Ser Asp Val Ser Gly Phe Asp Ala
    50                  55                  60

Pro Gln Arg Thr Ala Glu Tyr Ala Leu Gly Thr Ile Gly Val Leu Lys
65                  70                  75                  80

Ser Tyr Leu Glu Lys Thr Asn Asn Ile Thr Lys Ser Ile Ala Cys Gly
                85                  90                  95

Ser Leu Ile Thr Val Leu Gln Asn Leu Asp Val Gly Leu Val Ile Gln
```

-continued

```
        100                 105                 110

Ala Arg Asp Ser Asn Thr Glu Asp Thr Asn Tyr Leu Arg Ser Cys Asn
        115                 120                 125

Thr Ile Leu Ser Tyr Ile Asp Lys Ile His Lys Lys Arg Gln Ile Ile
    130                 135                 140

His Ile Leu Lys Arg Leu Pro Val Gly Val Leu Cys Asn Leu Ile Gln
145                 150                 155                 160

Ser Val Ile Ser Ile Glu Glu Lys Ile Asn Ser Ser Met Lys Thr Glu
                165                 170                 175
```